(12) United States Patent
Fonfe et al.

(10) Patent No.: US 10,399,934 B2
(45) Date of Patent: Sep. 3, 2019

(54) PROCESS FOR PREPARING AN ALKANESULPHONIC ACID

(71) Applicant: Evonik Degussa GmbH, Essen (DE)

(72) Inventors: Benjamin Fonfe, Frankfurt (DE); Nadine Duerr, Alsbach (DE); Harald Jakob, Hasselroth (DE); Chiu Kee Cheung, Alzenau (DE); Andreas Doerflein, Grosskrotzenburg (DE); Sebastian Fuss, Flieden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/778,802

(22) PCT Filed: Nov. 30, 2016

(86) PCT No.: PCT/EP2016/079201
§ 371 (c)(1),
(2) Date: May 24, 2018

(87) PCT Pub. No.: WO2017/093279
PCT Pub. Date: Jun. 8, 2017

(65) Prior Publication Data
US 2018/0354897 A1    Dec. 13, 2018

(30) Foreign Application Priority Data

Nov. 30, 2015 (EP) .................................... 15197066

(51) Int. Cl.
| | | |
|---|---|---|
| *C07C 303/00* | (2006.01) | |
| *B01J 19/00* | (2006.01) | |
| *C07C 303/16* | (2006.01) | |
| *C07C 309/04* | (2006.01) | |
| *C07C 309/05* | (2006.01) | |

(52) U.S. Cl.
CPC ......... *C07C 303/16* (2013.01); *B01J 19/0006* (2013.01); *C07C 309/04* (2013.01); *C07C 309/05* (2013.01); *B01J 2219/0004* (2013.01); *B01J 2219/00707* (2013.01)

(58) Field of Classification Search
CPC ... C07C 303/16; C07C 309/04; C07C 309/05; B01J 19/006
See application file for complete search history.

(56) References Cited

U.S. PATENT DOCUMENTS

| | | |
|---|---|---|
| 2,489,318 A | 11/1949 | Proell |
| 4,987,250 A | 1/1991 | McGee et al. |
| 6,066,760 A | 5/2000 | Schon |

OTHER PUBLICATIONS

International Search Report and Written Opinion dated Feb. 21, 2017, in PCT/EP2016/079201, filed Nov. 30, 2016.
Casella, I. et al., "Amperometric detection of sulfur-containing compounds in Alkaline media", The Analyst, vol. 127, No. 5, Apr. 2, 2002, pp. 647-652.
Pavlova, A. et al., "Sulfur Compounds in Petroleum Hydrocarbon Streams", Petroleum & Coal, ISSN 1337-7027, vol. 54, XP055269474, 2012, pp. 9-13.
U.S. Appl. No. 15/103,784, filed Oct. 20, 2016, 2016/0304446, Fonfe et al.
U.S. Appl. No. 15/102,842, filed May 17, 2018, 2018/0133704, He et al.
U.S. Appl. No. 15/537,592, filed Jun. 19, 2017, Jakob et al.

*Primary Examiner* — Sikarl A Witherspoon
(74) *Attorney, Agent, or Firm* — Oblon, McClelland, Maier & Neustadt, L.L.P.

(57) ABSTRACT

The present invention relates to a process for preparing alkanesulphonic acid by oxidizing an alkyl mercaptan, a dialkyl disulphide and/or a dialkyl polysulphide having three to nine sulphur atoms with an oxidizing agent, wherein additional oxidizing agent is fed into the oxidation if as yet unoxidized alkyl mercaptan and/or unoxidized dialkyl disulphide and/or at least one intermediate from the oxidation of the dialkyl disulphide and/or of the dialkyl polysulphide is present in the reaction output, and a corresponding apparatus for performance of oxidation reactions.

17 Claims, 9 Drawing Sheets

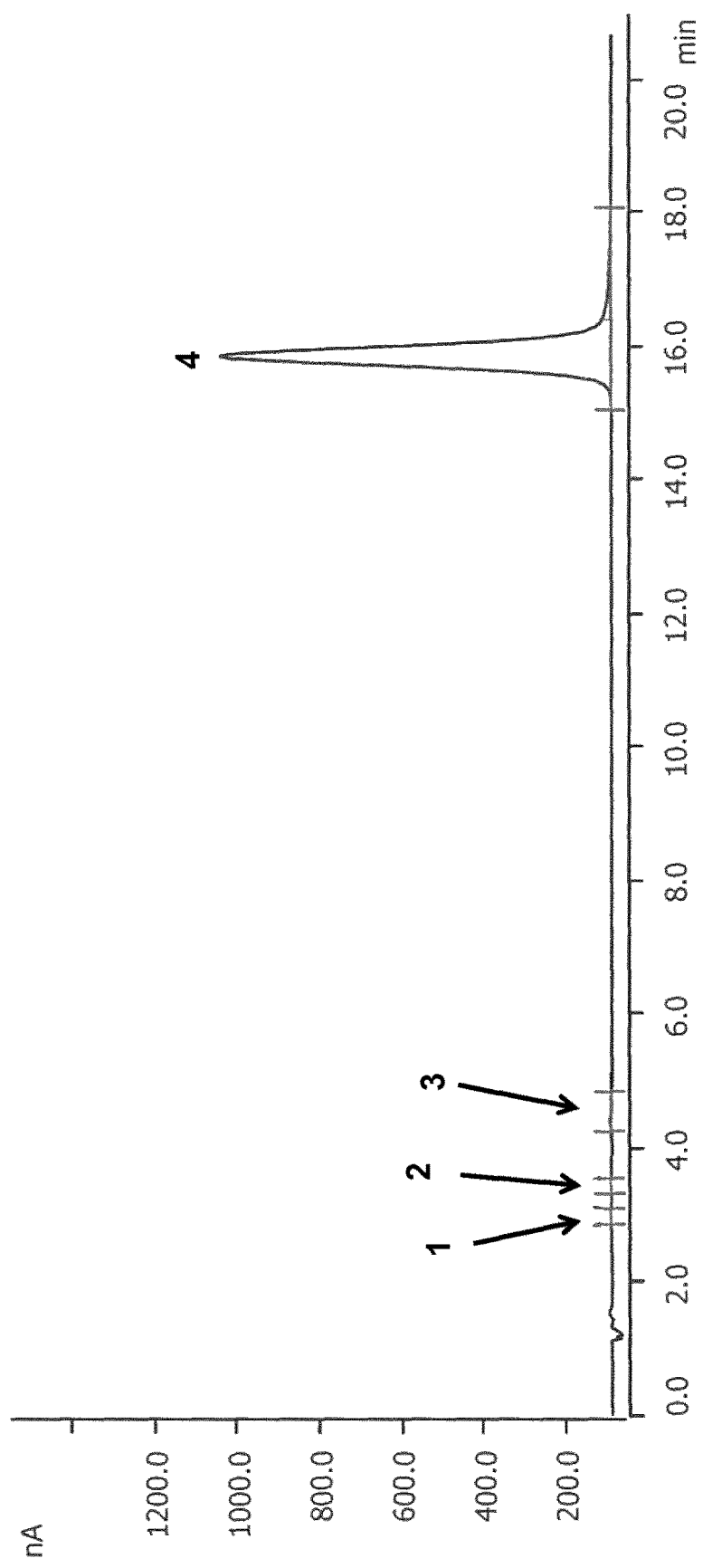
Fig. 1 Chromatogram of Comparative Example 1

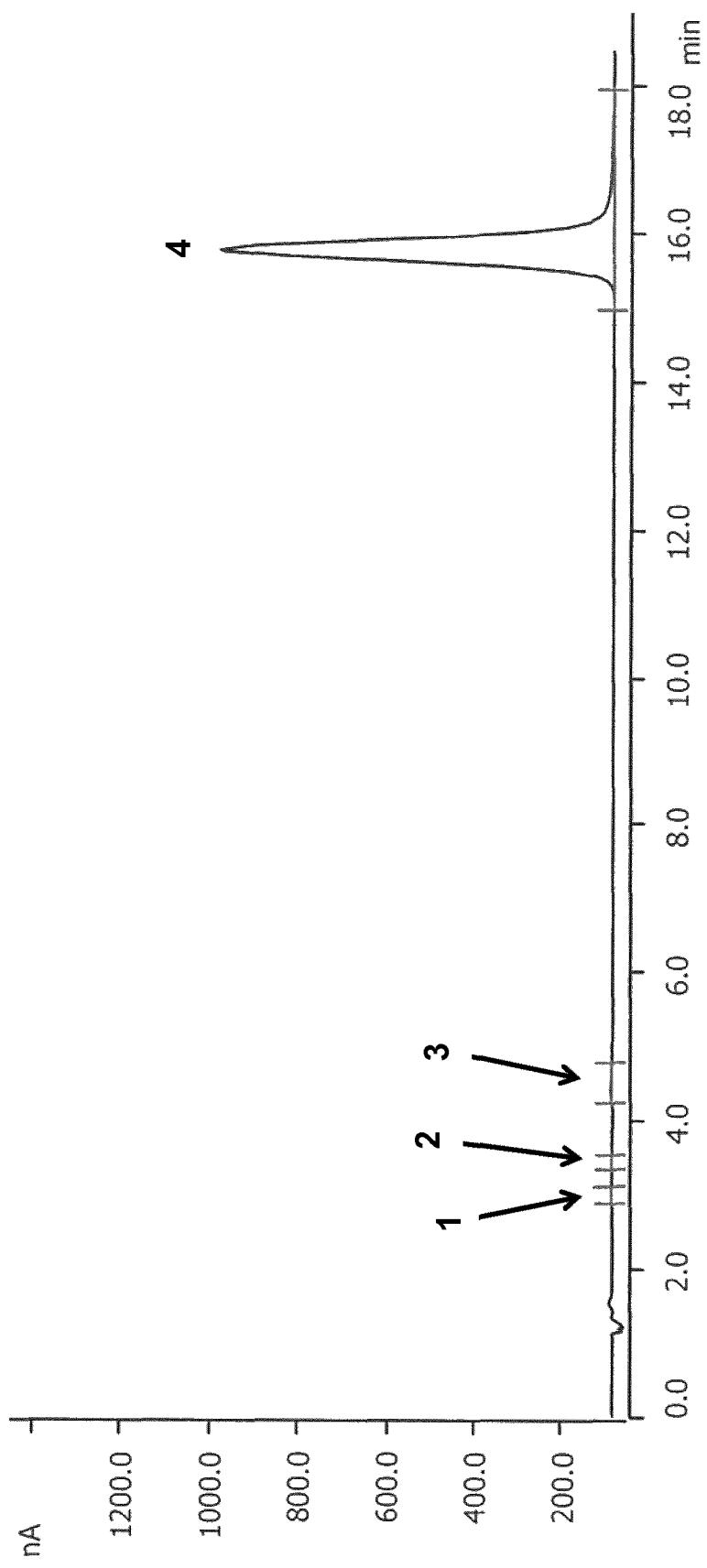
Fig. 2: Chromatogram of Comparative Example 2

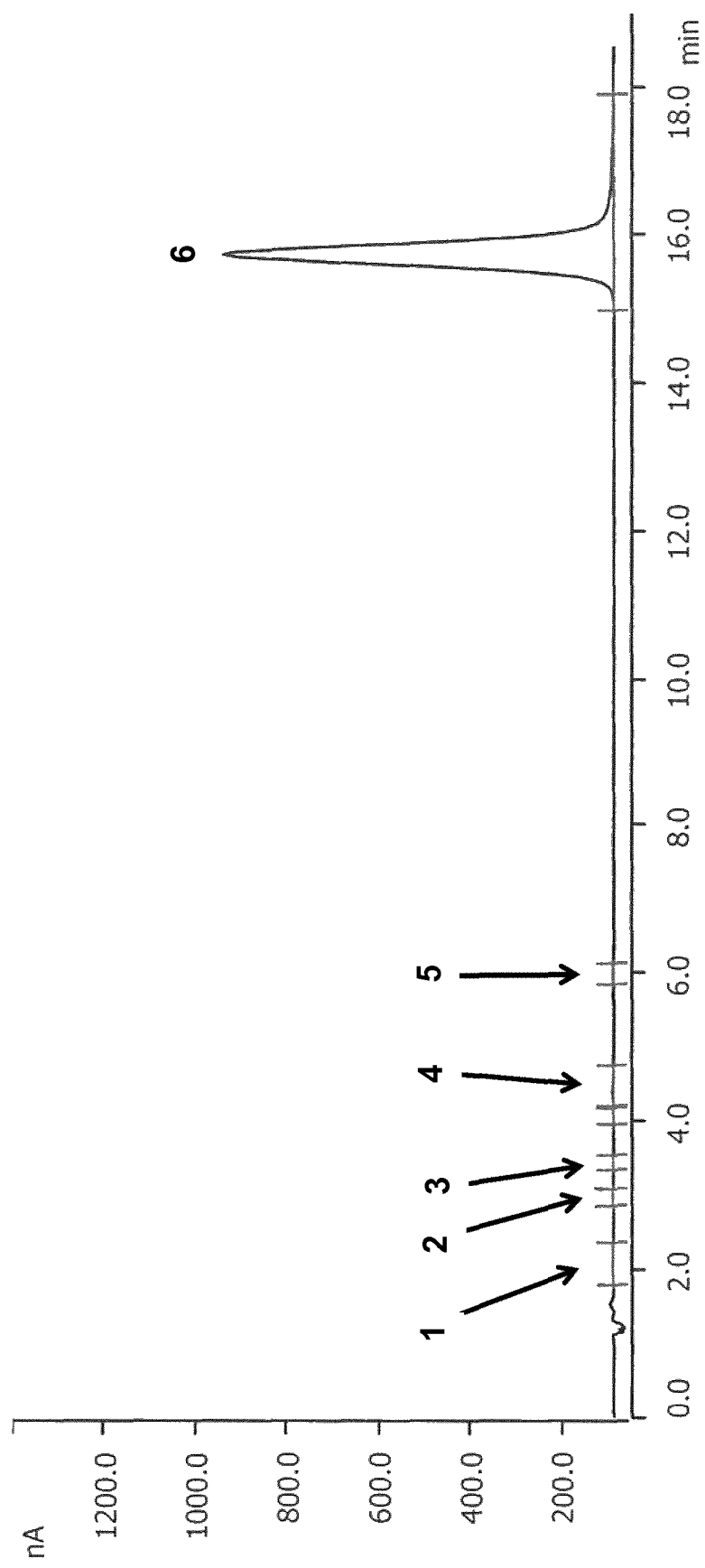

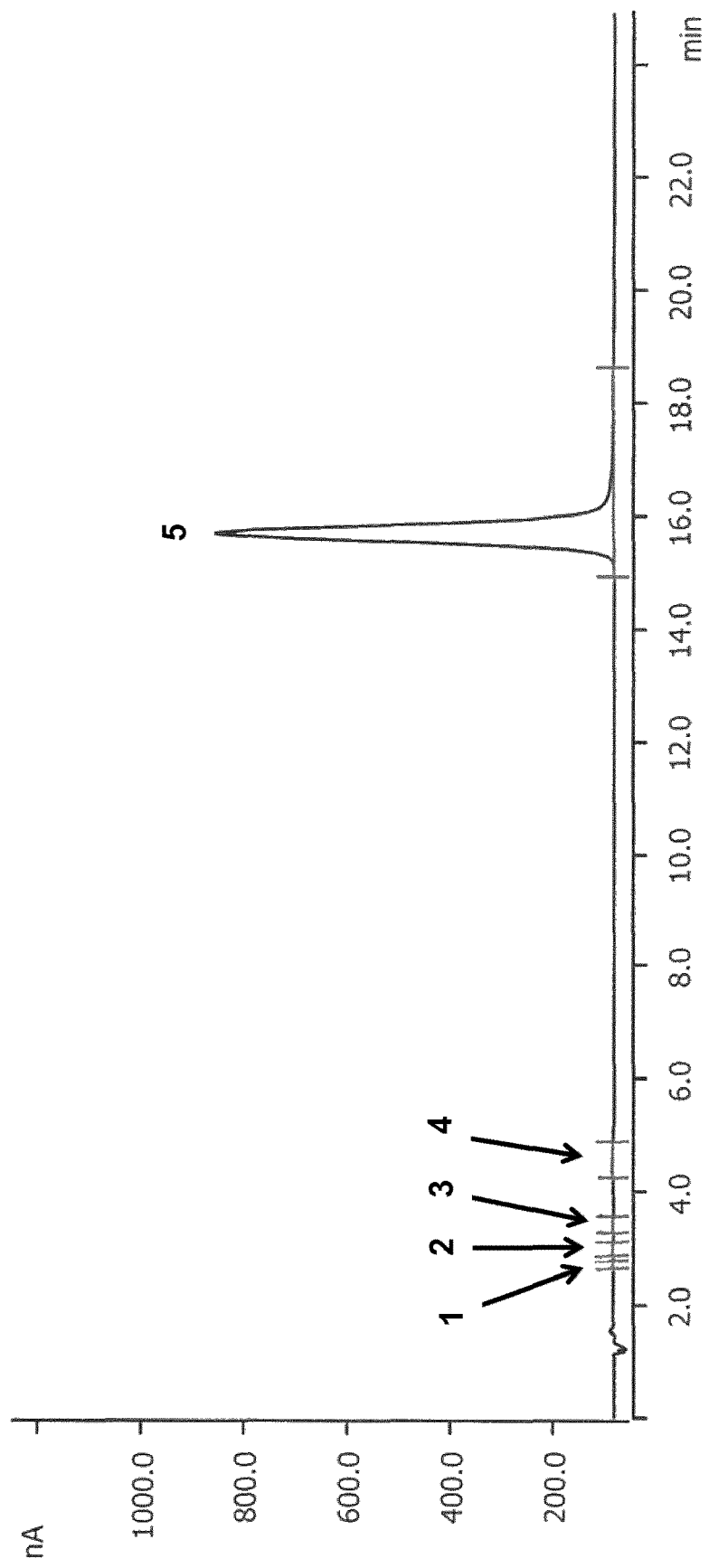
Fig. 4: Chromatogram of Comparative Example 4

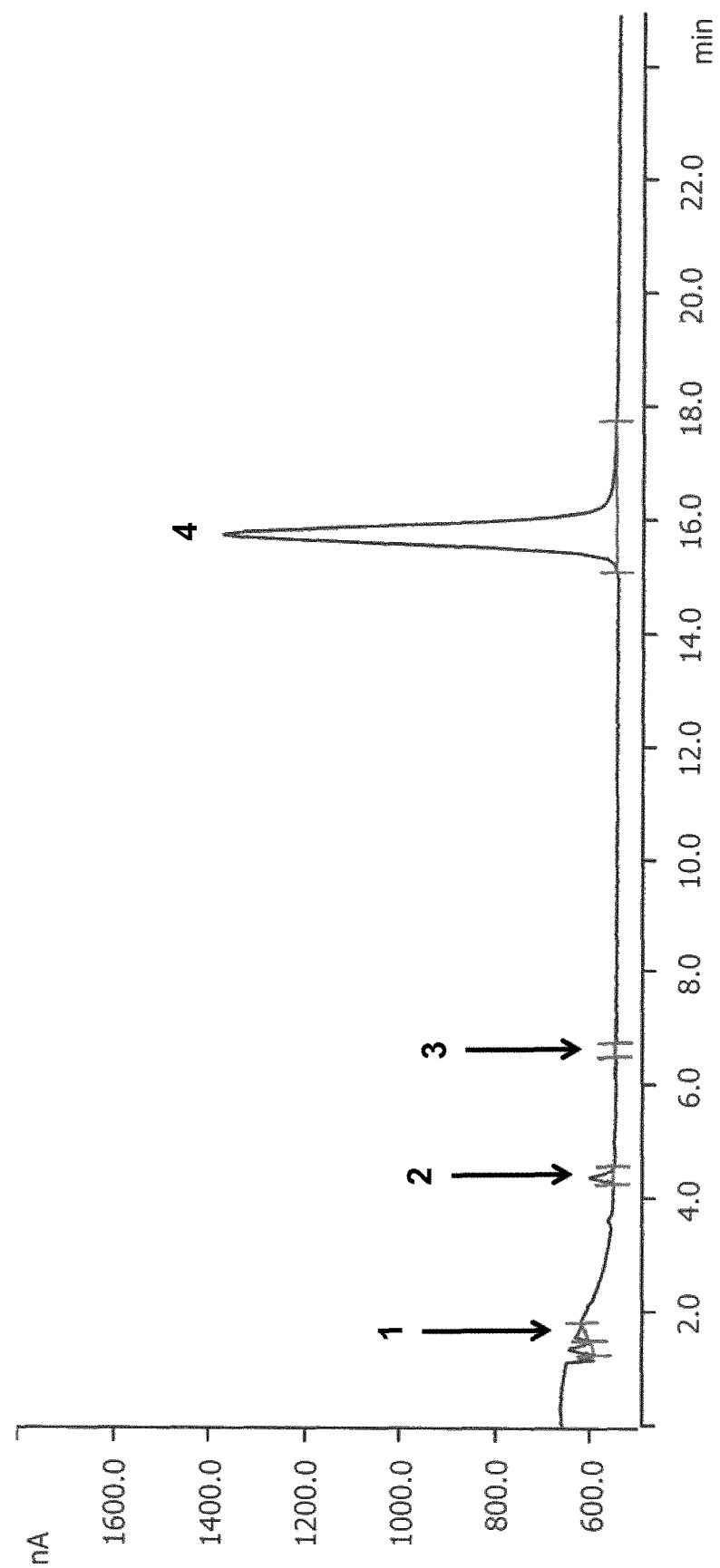

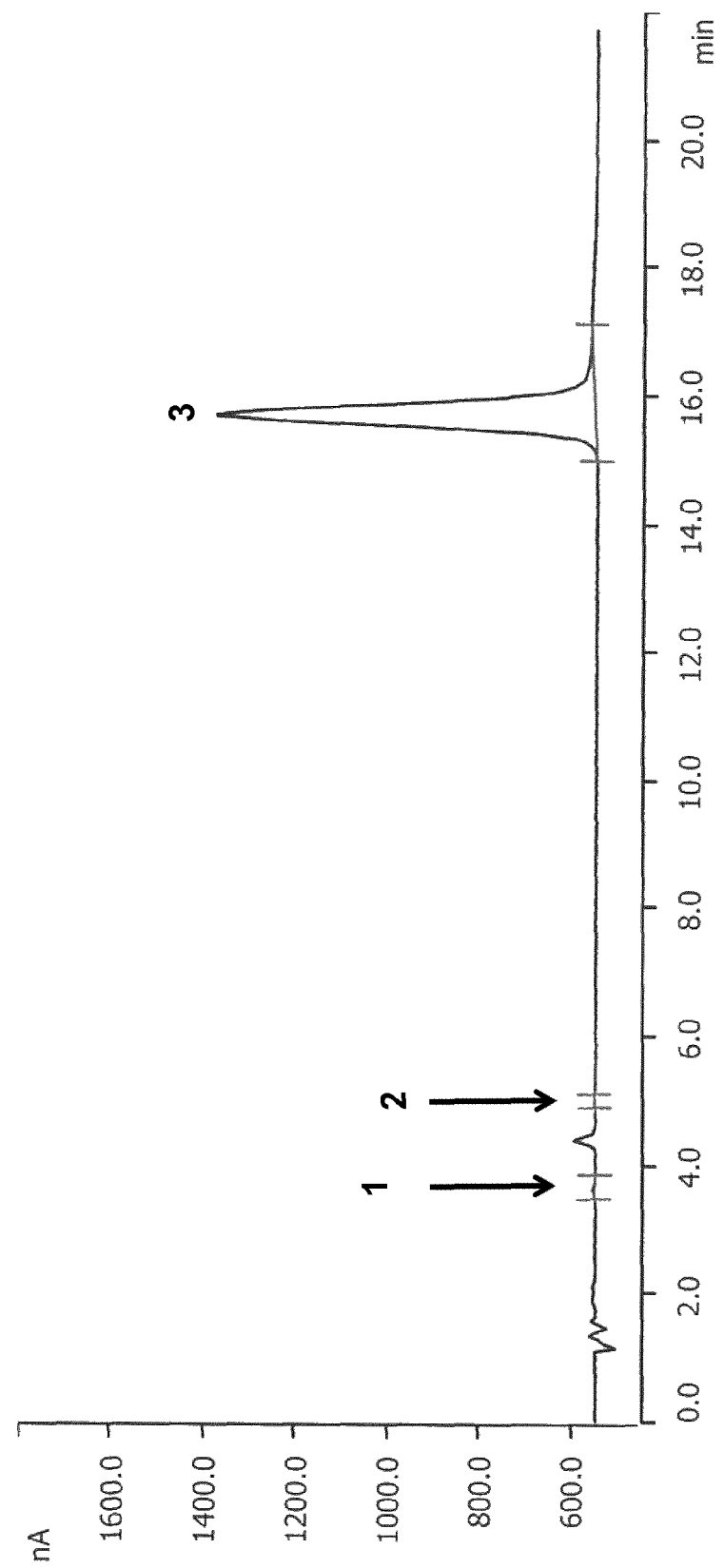
Fig. 6: Chromatogram of Example 2

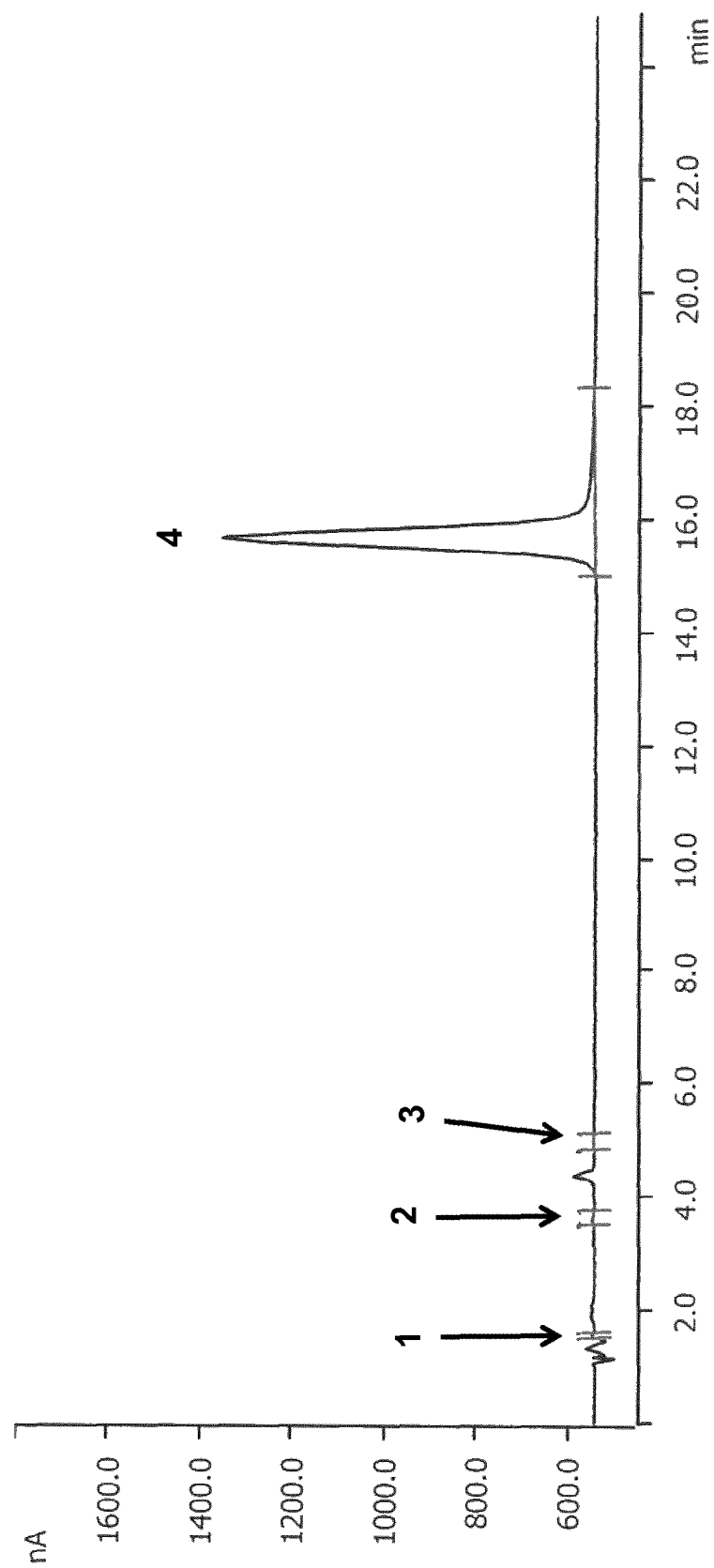
Fig. 7: Chromatogram of Example 3

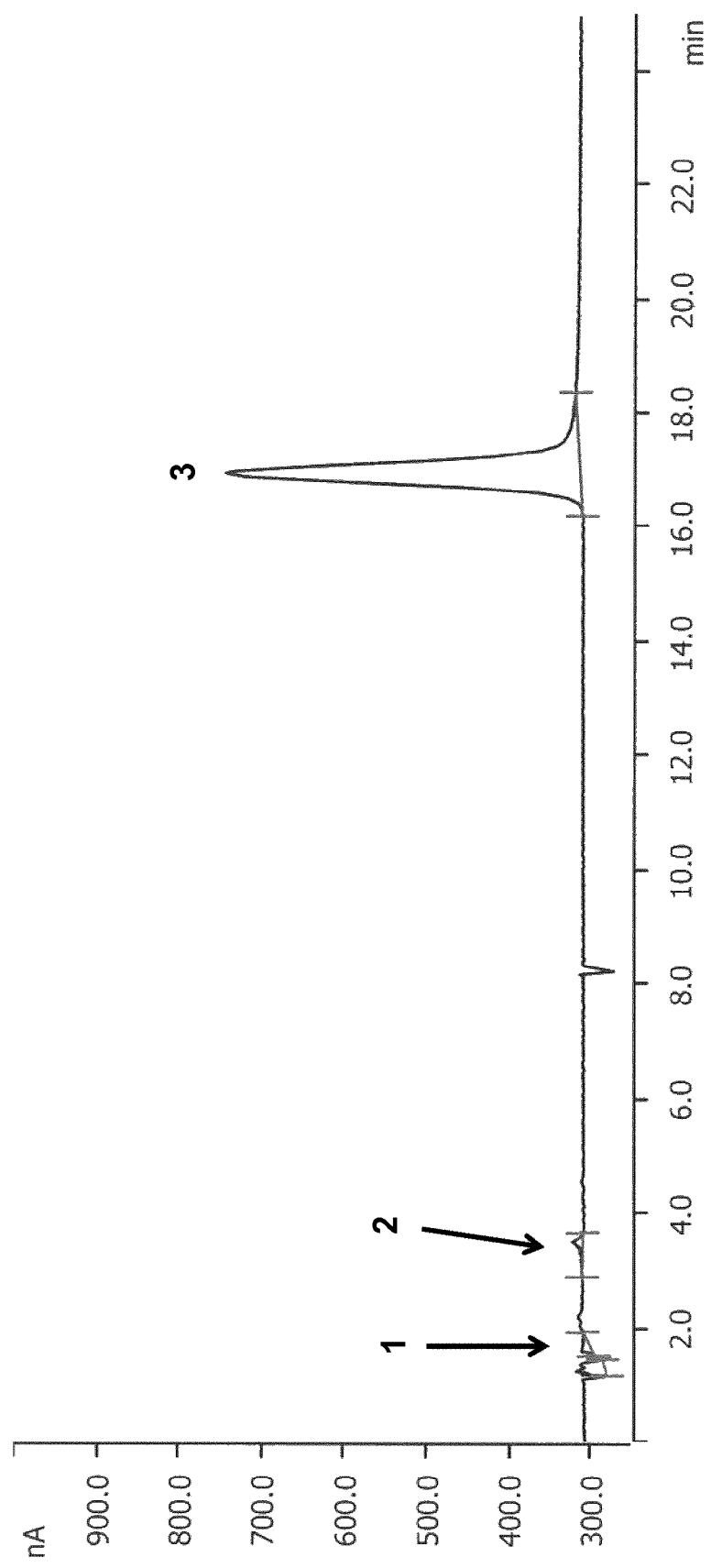
Fig. 8: Chromatogram of Example 4

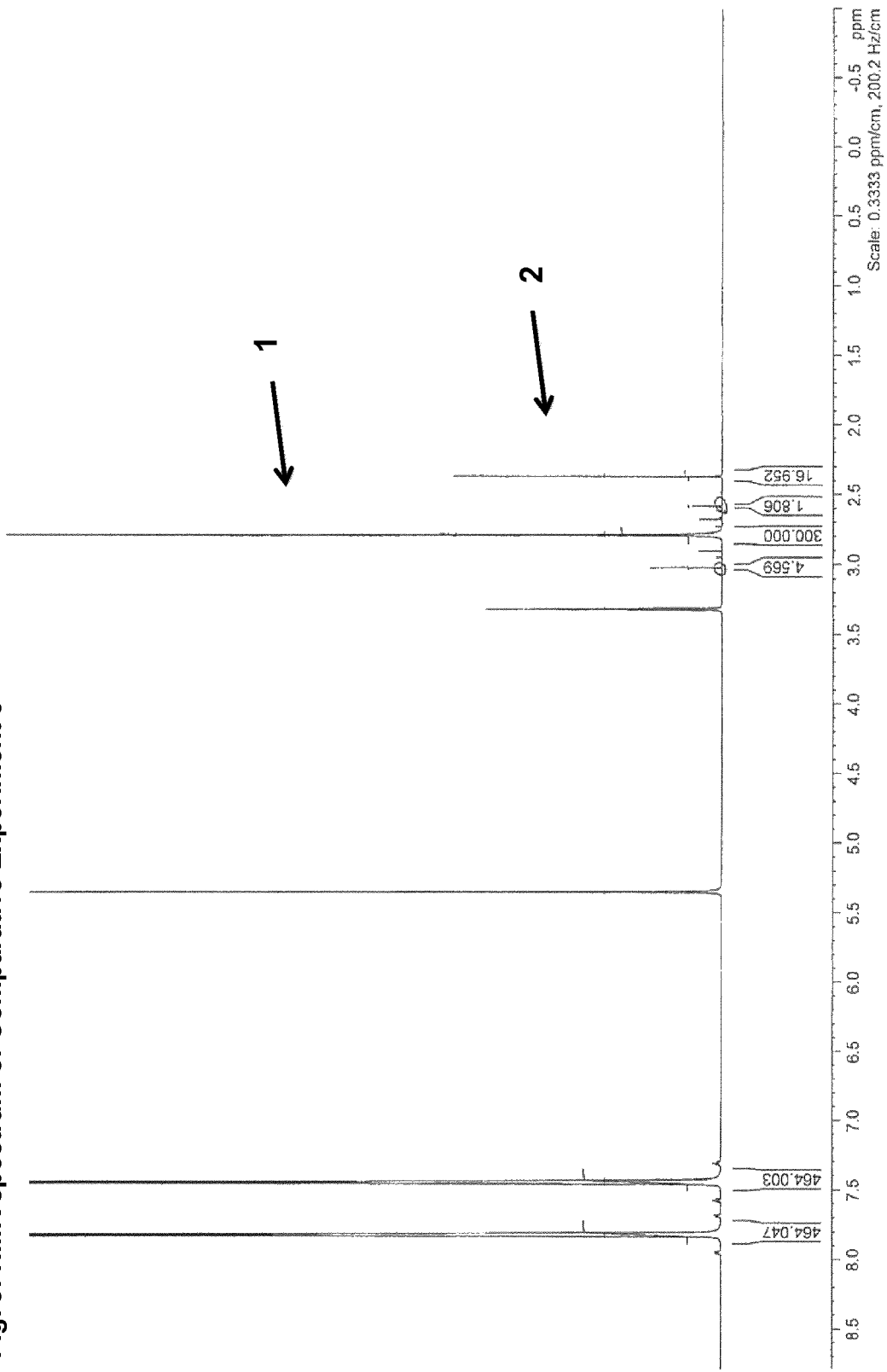
Fig. 9: NMR spectrum of Comparative Experiment 5

PROCESS FOR PREPARING AN ALKANESULPHONIC ACID

The present invention relates to a process for preparing an alkanesulphonic acid by oxidizing an alkyl mercaptan, a dialkyl disulphide and/or a dialkyl polysulphide having three to nine sulphur atoms with an oxidizing agent, wherein additional oxidizing agent is fed into the oxidation if as yet unoxidized alkyl mercaptan and/or unoxidized dialkyl disulphide and/or at least one intermediate from the oxidation of the dialkyl disulphide and/or of the dialkyl polysulphide is present in the reaction output, and a corresponding apparatus for performance of oxidation reactions.

Sulphonic acids are organic derivatives of sulphuric acid, from which they differ structurally by the replacement of a hydroxyl group by an organic residue. The general structural formula of alkanesulphonic acids is therefore R—$SO_3$—H where R denotes an organic radical, for example alkyl or aryl. Depending on this organic radical, a distinction is made between aliphatic, olefinic and aromatic sulphonic acids. The free sulphonic acids are generally colourless and hygroscopic substances whose acid strength corresponds to that of the inorganic acids. With a pKa of −5.5, trifluoromethanesulphonic acid is actually one of the strongest known acids and therefore belongs to the group of so-called superacids. In contrast to the sulphate salts of mercury, lead and silver, the corresponding sulphonates have very good water solubility.

The prior art, for example publications WO 98/34914 A1, U.S. Pat. No. 2,433,395, 2,433,396, 2,498,318, 2,502,618, 2,505,910, 2,697,722, 2,727,920, WO 00/31027 A1 and CN 101648892 A, discloses a multitude of processes for industrial scale preparation of alkanesulphonic acids by oxidation of alkyl mercaptan, dialkyl disulphides and dialkyl polysulphides. If the process in question proceeds from an alkyl mercaptan, this mercaptan is oxidized to the corresponding dialkyl disulphide, which is subsequently oxidized further to the alkanesulphonic acid. According to the view expressed in the literature, the oxidation of dialkyl disulphides R—S—S—R to the corresponding alkanesulphonic acids proceeds via the intermediates of an alkanesulphoxide S-alkyl ether R—S—SO—R, an S-alkyl alkanesulphonate R—S—$SO_2$—R, an alkanesulphoxide S-alkylthiosulphonate R—SO—$SO_2$—R and a dialkyl disulphone R—$SO_2$—$SO_2$—R, the latter ultimately being hydrolysed to give the desired alkanesulphonic acid R—$SO_3$—H. In the preparation of alkanesulphonic acids by oxidation of dialkyl polysulphides having three or more sulphur atoms, the formation of alkyl disulphides and alkyl mercaptans and the subsequent oxidation thereof, corresponding to the oxidation of dialkyl disulphides and alkyl mercaptans, are discussed in the literature.

For a maximum yield of alkanesulphonic acid, the aim is complete conversion of the respective starting materials to the alkanesulphonic acid. In the prior art, it is therefore usual to work with an excess of nitric acid as oxidizing agent, as described, for example, in WO 00/31027. As a result of the high proportion of nitric acid in the reaction mixture, however, considerable amounts of water are also introduced into the reaction, and the water subsequently has to be separated from the desired product in an energy-intensive and costly manner. A further disadvantage of this process is the formation of large amounts of nitrogen oxides that are harmful to health and damaging to the environment, of which dinitrogen oxide $N_2O$ is also considered to be a so-called greenhouse gas. To avoid the release of these nitrogen oxides, appropriate measures therefore have to be taken, which are likewise costly and energy-intensive. This makes the oxidation of alkyl mercaptans, dialkyl disulphides and/or dialkyl polysulphides with an excess of nitric acid to alkanesulphonic acids economically unattractive under overall consideration.

Alternatively, therefore, the oxidation of alkyl mercaptans, dialkyl disulphides and/or dialkyl polysulphides to alkanesulphonic acids is also conducted with air and a substoichiometric amount of nitric acid as catalyst. In the case of this procedure, however, it has to be ensured that sufficient air, oxygen-enriched air or even pure oxygen is fed into the reaction as oxidizing agent, in order to ensure maximum oxidation of the starting materials and intermediates to the alkanesulphonic acid. If this is not ensured, the starting materials and/or the oxidation intermediates are oxidized only incompletely, if at all, to the desired alkanesulphonic acid. In this case, large amounts of unconverted starting materials and/or oxidation intermediates have to be separated from the crude alkanesulphonic acid and recycled into the reaction.

However, the resulting lack of economic efficiency is still a comparatively minor problem. What is more problematic is that elemental sulphur precipitates out in the case of incomplete conversion of the oxidation intermediates to the alkanesulphonic acid. This precipitate occurs particularly at temperatures of more than 90° C. and is therefore a serious problem particularly for a distillation of the reaction mixture conducted at temperatures of well over 90° C. This is because, even in small amounts, this sulphur precipitate blocks the components of the distillation column through which the distillate flows, such as conduits and column heads, which leads to operation shutdowns and hence inevitably to production outages. It is suspected that this sulphur precipitate is attributable to the breakdown of sulphur-containing oxidation products, possibly accompanied by synproportionation of sulphur atoms of different oxidation states, with release of elemental sulphur.

Typically, a production plant is not always operated at the same load. Instead, the load of a plant varies as a function of the demand for and amount of starting materials used. In addition, varying process parameters such as temperature and pressure can also affect the degree of conversion to the alkanesulphonic acid.

In order always to ensure a constantly high conversion to the alkanesulphonic acid and the avoidance of a sulphur precipitate, even in the case of different loads of a production plant and varying process parameters, there is therefore a need for a suitable process control regime.

This object is achieved in accordance with the invention by determining a sulphur-containing starting compound, preferably an alkyl mercaptan, dialkyl disulphide and/or dialkyl polysulphide having three to nine sulphur atoms, that has not been reacted or not completely reacted to the alkanesulphonic acid, and/or an oxidation intermediate from the oxidation of a dialkyl sulphide and/or dialkyl polysulphide to the alkanesulphonic acid in the reaction output from the oxidation reaction and, in the case of presence thereof in the reaction output from the oxidation reaction, feeding additional oxidizing agent into the oxidation reaction. In this way, the oxidation reaction to give the desired alkanesulphonic acid is completed.

The present invention therefore provides a process for preparing an alkanesulphonic acid, comprising the steps of
a) oxidizing at least one sulphur-containing starting compound with an oxidizing agent to give the corresponding alkanesulphonic acid, wherein the sulphur-containing starting compound is selected from the group consisting of an alkyl mercaptan, a dialkyl disulphide and a dialkyl polysulphide having three to nine sulphur atoms, b) determining at least one sulphur-containing starting compound and/or at least one oxidation intermediate from the oxidation of the sulphur-containing starting compound to the corresponding alkanesulphonic acid in the reaction output from step a), and c) supplying additional oxidizing agent in step a) to complete the oxidation reaction when, in step b), a sulphur-containing starting compound and/or an oxidation intermediate from the oxidation of the sulphur-containing starting compound to the corresponding alkanesulphonic acid has been determined.

In the context of the present invention, the terms alkyl mercaptan, dialkyl disulphide and dialkyl polysulphide are used in accordance with the common knowledge of the person skilled in the art. Therefore, an alkyl mercaptan corresponds to the general formula R—SH, a dialkyl disulphide to the general formula R—S—S—R, and a dialkyl polysulphide to the general formula R—$S_n$—R with n=3 to 9, where R is an alkyl group. Typically, the alkyl groups of the alkyl mercaptans, dialkyl disulphides or dialkyl polysulphides used in the context of the present invention have 1 to 12 carbon atoms. With respect to the size and structure of these alkyl groups, for example with regard to additional functional groups, the process according to the invention is not subject to any restrictions, provided that it is ensured that the functional groups of the alkyl groups are themselves unreactive under the reaction conditions that prevail in the oxidation reaction, and the sulphur-containing compounds in question are at least partly soluble in the solvent used. The solvent in the process according to the invention may also be the alkanesulphonic acid to be prepared itself. Therefore, the alkyl mercaptans, dialkyl disulphides and/or dialkyl polysulphides may have linear or branched alkyl groups, preferably linear, each having 1 to 12 carbon atoms, preferably 1 to 6 or 1 to 4 carbon atoms. More preferably, the alkyl groups are selected from the group consisting of methyl, ethyl, n-propyl, isopropyl, n-butyl, iso-butyl and tert-butyl.

The most important alkanesulphonic acid from an economic point of view is methanesulphonic acid, since the metal salts thereof are used in large amounts as electrolytes in methanesulphonic acid electrolysis baths in the production of circuits for the electronics industry. In addition, methanesulphonic acid is finding increasing use as a constituent of detergents since it can easily be integrated into detergent solutions due to its lack of colour and odour. A further important new field of use for methanesulphonic acid is use in oil drilling: The mineral oil-bearing strata that are made accessible by drill holes often release the oil only in a limited mass, if at all. To achieve enhanced release of the oil, therefore, the mineral oil-bearing rock strata are softened with methanesulphonic acid. Furthermore, methanesulphonic acid also finds use as a catalyst in a multitude of organic reactions, such as alkylations, esterifications, polymerizations or heterocyclic syntheses, or in the formation of acid addition salts with basic active ingredients.

Preferably, therefore, the sulphur-containing starting compound in the process according to the invention is methyl mercaptan, dimethyl disulphide and/or dimethyl polysulphide having three to nine sulphur atoms, and the alkanesulphonic acid to be prepared is methanesulphonic acid.

When the sulphur-containing starting compound is dimethyl disulphide and/or dimethyl polysulphide, the process according to the invention is preceded by a separate preparation of dimethyl disulphide and/or dimethyl polysulphide, preferably by reaction of methyl mercaptan with elemental sulphur. The hydrogen sulphide formed at the same time is recycled into the process in question for preparation of methyl mercaptan.

In the process according to the invention, the sulphur-containing starting compounds can be supplied individually or in a mixture to the oxidation reaction of step a). In the case of use of sulphur-containing starting compounds having two alkyl groups, preference is given to dialkyl disulphides and dialkyl polysulphides having identical alkyl groups; these compounds are also referred to in the context of the present invention as symmetric dialkyl disulphides or symmetric dialkyl polysulphides. The performance of the process according to the invention with symmetric dialkyl disulphides or dialkyl polysulphides leads to a single alkanesulphonic acid, which significantly eases the workup of the product mixture. By contrast, the use of unsymmetric dialkyl disulphides and/or unsymmetric dialkyl polysulphides leads to a mixture of alkanesulphonic acids which, in some cases, can be separated into the individual alkanesulphonic acids only with a considerable degree of complexity. Preference is therefore given to using, in the process according to the invention, symmetric dialkyl disulphides or dialkyl polysulphides. In the case of use of different starting compounds, for example an alkyl mercaptan and a dialkyl disulphide, therefore, the alkyl groups in these compounds are preferably likewise identical.

In the case of use of an alkyl mercaptan as starting compound, the alkyl mercaptan is first oxidized to the corresponding dialkyl disulphide. The dialkyl disulphide thus obtained or used directly as starting compound, and correspondingly also a dialkyl polysulphide, is subject to a series of individual oxidation steps in the course of oxidation to the alkanesulphonic acid, which result in stepwise transfer of oxygen atoms to the sulphur atoms, and this leads to formation of derivatives of the dialkyl disulphide or dialkyl polysulphide in question having at least one oxygen bonded to a sulphur. In the case of a dialkyl disulphide R—S—S—R, this stepwise oxidation proceeds via the intermediates, discussed in the literature, of an alkanesulphoxide S-alkyl ester R—S—SO—R, an alkanesulphonic acid S-alkyl ester R—S—$SO_2$—R or a dialkyl disulphoxide R—SO—SO—R or an alkanesulphoxide S-alkyl thiosulphonate R—SO—$SO_2$—R and a dialkyl disulphone R—$SO_2$—$SO_2$—R. Finally, in the presence of water, one equivalent of the dialkyl disulphone is converted to two equivalents of the corresponding alkanesulphonic acid.

During the oxidation of a dialkyl disulphide to the alkanesulphonic acid, all these intermediates are present either simultaneously or successively in the reaction mixture of step a).

If the oxidizing agent required for the oxidation of a sulphur-containing starting compound to the corresponding alkanesulphonic acid is present in deficiency based on the amount of the sulphur-containing starting compound used, both the sulphur-containing starting compound and the intermediates of the oxidation reaction are oxidized either not at all or incompletely to the desired alkanesulphonic acid. This has a direct negative effect on the yield of the desired alkanesulphonic acid. In a complex workup, it is then necessary to separate the at least one unconverted starting compound and the oxidation intermediates from the alkanesulphonic acid and recycle them into the oxidation reaction. This is associated with considerable additional capital and operating costs.

In order to achieve a maximum yield of the desired alkanesulphonic acid and simultaneously to avoid accumulation of oxidation intermediates in the reaction mixture, it is therefore absolutely necessary, at regular intervals and preferably continuously, to determine sulphur-containing starting compounds and/or oxidation intermediates in the reaction output from step a) (step b)) and, in the event of their presence, supply additional oxidizing agent to step a) for completion of the oxidation reaction (step c)). On the basis of the determination of the sulphur-containing starting compounds and/or oxidation intermediates in the reaction output from step a), the amount of additional oxidizing agent required to complete the oxidation in step a) is determined. Preferably, the amount of additional oxidizing agent supplied in step a) is at least that required to complete the oxidation reaction. More particularly, the amount of the additional oxidizing agent supplied in step c) is greater than the amount of additional oxidizing agent required to complete the oxidation in step a). This ensures completion of the oxidation reaction.

The industrial scale separation of a product mixture from the preparation of alkanesulphonic acids by oxidation of sulphur-containing starting compounds is generally effected by a distillation, which is associated with considerable capital and energy costs. More particularly, the energy costs are considerable considering the high temperatures required for overhead distillation of the alkanesulphonic acid in question. Even the simplest representative of the alkanesulphonic acids, methanesulphonic acid, has a boiling point of 167° C. at 13 hP.

Temperatures of more than 90° C., however, are highly problematic when the oxidation of sulphur-containing starting compounds to the corresponding alkanesulphonic acid has not proceeded at all or has not proceeded completely. This is because precipitation of elemental sulphur is observed at temperatures of more than 90° C. for the respective reaction or product mixtures. Even small amounts of precipitated sulphur can both block the pipelines leading away from the reactor and the column heads and conduits of distillation units, which inevitably leads to plant shutdowns and hence to production shutdowns. It is suspected that the sulphur precipitate is attributable to breakdown of the oxidation intermediate alkanesulphonic acid S-alkyl ester and possibly a synproportionation of the sulphur atoms of different oxidation states, which presumably accumulates in the reaction mixture in the event of an incomplete oxidation of sulphur-containing starting compounds to the desired alkanesulphonic acids. To avoid plant and production shutdowns, it is therefore necessary to determine the presence of alkanesulphonic acid S-alkyl esters in the reaction output from step a) at least at regular intervals and preferably continuously and, in the case that alkanesulphonic acid S-alkyl esters are present in the reaction output from step a), to supply additional oxidizing agent to complete the oxidation in step a).

In one embodiment of the process according to the invention, therefore, in step b), an alkanesulphonic acid S-alkyl ester is determined as oxidation intermediate.

Since, in the process according to the invention, preference is given to using mercaptan, dimethyl disulphide and/or dimethyl polysulphides as sulphur-containing starting compounds, the oxidation intermediate determined in step b) of the process according to the invention is preferably S-methyl methanesulphonate or methyl methanethiosulphonate (MMTS).

In the context of the present invention, it has been found that oxidation intermediates from the preparation of alkanesulphonic acids, especially oxidized dialkyl disulphides or dialkyl polysulphides having one or more oxygen atoms on a sulphur atom, can be determined reliably and precisely with the aid of UV-vis spectroscopy. S-Alkyl alkanesulphonates in particular are suitable for determination by means of UV-vis spectroscopy because of their strongly polar ester group. By contrast, it is virtually impossible to determine alkanesulphonic acids with the aid of UV-vis spectroscopy. Consequently, UV-vis spectroscopy enables reliable determination of intermediates from the oxidation of dialkyl disulphides or dialkyl polysulphides to the alkanesulphonic acid, especially in a matrix containing the corresponding alkanesulphonic acid, in which the alkanesulphonic acid present does not impair the determination of the S-alkyl alkanesulphonates.

In one embodiment of the process according to the invention, the oxidation intermediate, especially the S-alkyl alkanesulphonate, is determined in step b) by means of UV-vis spectroscopy.

The term "UV-vis spectroscopy" is used in accordance with the common art knowledge of the person skilled in the art and refers in its most general form to a method which utilizes the electromagnetic waves of ultraviolet (UV) and visible (vis) light to determine compounds which absorb light in the UV and/or visible region. A UV-vis spectrometer used for this determination contains a light source with a slit, a prism for monochromatization, a cuvette with a sample containing the compound to be determined, a detector and an amplifier. A single-beam UV-vis spectrometer contains only one cuvette with a sample containing the compound to be determined. The way in which a single-beam UV-vis spectrometer works can be described as follows: The light source emits ultraviolet, visible and near infrared light in the wavelength range from 200 nm to 1100 nm. In the monochromator, the wavelength of light chosen for measurement is selected, and the monochromatic light passes through the cuvette with the sample in question. The detector measures the intensity of the light which has passed through the irradiated body. In this measurement, however, it is also possible for light to be absorbed by the solvent or, if the determination is preceded by a chromatographic separation, the eluent of the sample, or for light to be reflected or scattered at the cuvette. In all cases, this would lead to attenuation of the intensity of the light that has passed through the irradiated body, which would have a distinct effect on the quality of the determination. Therefore, prior to every measurement of the sample in question in a single-beam spectrometer, a comparative measurement is first conducted with a cuvette containing only the solvent of the sample and, if the determination is preceded by a chromatographic separation, the eluent of the sample as well. The value obtained for the comparative measurement is saved and then the sample is analysed. The intensities measured for the comparative measurement and the sample are compared in the amplifier, and the amplifier then adjusts the intensity of the light beam for the measurement solution by means of a slit to the intensity of the comparative measurement. In the case of a twin-beam spectrometer, the monochromatic light hits a sector mirror which alternately allows the light to fall through the measurement solution and the comparative solution. The two solutions are in cuvettes. The two light beams are received in the detector and the intensities are compared in the amplifier. The amplifier then adjusts the intensity of the light beam from the comparative solution to the intensity of the light beam from the measurement solution by introducing a comb aperture.

The attenuated intensity of the light of wavelength λ that has passed through the irradiated body, which is measured by the detector, is also referred to as extinction $E_\lambda$ and is a measure of the absorption of the compound to be determined for the light of wavelength λ. The weakening of radiation intensity with the path length in the passing through an absorbing substance is described by the Beer-Lambert Law: The extinction $E_\lambda$ (absorbance of the substance for light of wavelength λ) is given by $$E_\lambda = lg(I_0/I) = \varepsilon_\lambda \cdot c \cdot d,$$

with
I=intensity of the light passing (transmitted through) the sample (unit: $W \cdot m^{-2}$)
$I_0$=intensity of the incident (radiated) light (unit: $W \cdot m^{-2}$)
D=path length through the irradiated body (unit: m)
c=molar concentration of the absorbing compound in the liquid (unit: $mol^{-1}$)
$E_\lambda$=decadic extinction coefficient (often also referred to as spectral absorption coefficient) at wavelength λ. This is a parameter specific to the absorbing substance and can depend upon factors including the pH or the solvent. In the case of a concentration figure in mol, $\varepsilon_\lambda$ is reported as the decadic molar extinction coefficient, for example in the unit $m^2 \cdot mol^{-1}$.

The determination of S-methyl methanesulphonate is effected at a wavelength of 210 nm with a range of +/−5 nm and a measurement duration of 300 ms.

In contrast to the S-alkyl alkanesulphonates, UV-vis detection does not lead to satisfactory results in the case of sulphur-containing starting compounds, especially dialkyl disulphides and dialkyl polysulphides. For example, the use of a high performance liquid chromatograph (HPLC) with a UV detector allows the determination of dimethyl disulphide only within an error of about 10% at 1% by weight of dimethyl disulphide. Analysis by means of so-called headspace gas chromatography (GC), in which only the headspace above the sample is analysed and hence the analyte is barely affected, is unsuitable for the determination of dialkyl disulphides or dialkyl polysulphides. This is because this method allows good results only in synthetic samples but does not lead to satisfactory results in the determination of dialkyl disulphides in a real sample matrix. Nor does a switch from high-performance liquid chromatography to ion chromatography (IC) achieve any improvements, since dialkyl disulphides such as dimethyl disulphide cannot be determined with the required precision using a UV detector. This also applies to the use of a conductivity detector and a refractive index detector for determining dialkyl disulphides. In routine operation, detection limits of about 0.1% by weight are achievable by NMR analysis (nuclear magnetic resonance). However, this detection limit is too high for use in the determination dialkyl disulphides and dialkyl polysulphides in a matrix, especially in an alkanesulphonic acid matrix. A further disadvantage of nuclear spin resonance is that NMR spectrometers are highly sophisticated, costly and maintenance-intensive analytical instruments whose use directly in the vicinity of a production plant is impractical. Moreover, the complexity involved in achieving a relatively low detection limit by means of nuclear spin resonance is simply too large for use as a routine analysis instrument. The same limitations relating to detection limit also apply to NIR analysis (near infrared spectroscopy). In the context of the present invention, it has been found that pulsed amperometric detection is suitable for the determination of the sulphur-containing starting compound in step b).

In one embodiment of the process according to the invention, the sulphur-containing starting compound is therefore determined in step b) by means of pulsed amperometric detection.

Amperometric detection or amperometry is an electrochemical method for the quantitative determination of chemical compounds. A basic prerequisite for the applicability of amperometry is that the chemical compounds to be determined are readily oxidizable or reducible substances. The construction of the detector cell in which the measurement takes place is based on what is called a potentiostatic measurement arrangement. Therefore, a corresponding detector cell has three electrodes: a working electrode which serves to monitor the electrochemical processes, an auxiliary electrode which transports the current from the oxidation or reduction, and a reference electrode which is switched at high impedance and thus provides a uniform voltage at the working electrode; the current flow between working and auxiliary electrode is thus measured. If the required potential for an oxidation or reduction of the organic compound in question is present at the working electrode, a signal current is measured as a consequence of this electrochemical reaction. The measured electrolysis current is subsequently amplified and presented in a chromatogram as a function of time. Since the electrolysis current is directly proportional to the concentration of the unreacted organic compounds in the electrolysis reaction, the amperometric detection allows the determination of unknown concentrations of a specific organic compound with the aid of a previously generated calibration function. In the context of the present invention, amperometric detection in which only the potential required for carrying out the electrolysis reaction of the organic compound is applied at the working electrode is referred to as amperometric detection at constant potential.

For the objective underlying the present invention, however, it has been found that amperometric determination at constant potential still does not permit reproducible results for the determination of a dialkyl disulphide in an alkanesulphonic acid: In general, the value determined for the electrolysis current in the case of a repetition of a prior measurement is much lower than in the first measurement; for example, the measurement may decrease by more than 20% over a period of one hour. This is attributed firstly to the (partial) coverage of the working electrode with at least one adsorbate and to the occurrence of capacitive currents. The at least one adsorbate may be a product of the electrochemical reaction which has taken place at the working electrode. The occurrence of capacitive currents is probably caused by the formation of a diffusion layer at the working electrode or by hindrance of diffusion thereof into the solution, which is attributable to the redistribution of electroactive species in the detector cell due to typical convection processes.

According to the invention, the required accuracy and reproducibility of amperometric detection is achieved by virtue of it being pulsed. In the context of the present invention, pulsed amperometric detection is understood to mean amperometric detection in which the voltage applied to the working electrode for performance of the electrolysis is overlaid at periodic time intervals by at least one rectangular pulse. This rectangular pulse can be either an anodic or cathodic potential, and also a mixture of the two. By means of this technique, the working electrode is not only cleaned to remove the adsorbates adhering to its surface, but it is also conditioned for the next determinations. This conditioning improves the formation of the diffusion layer at the working electrode or diffusion thereof into the solution, which likewise contributes to a considerable improvement in the precision and reproducibility of the pulsed amperometric detection compared to a "simple" amperometric detection at constant voltage.

The electrolysis current measured in a pulsed amperometric detection is not just defined by the sulphur-containing starting compound to be determined, and more particularly by whether it is an alkyl mercaptan or a dialkyl disulphide or a dialkyl polysulphide, but also by its structure and its concentration. In order to be able to assure reliable and precise determination of the sulphur-containing compound used, for example of dimethyl disulphide, it is therefore necessary, prior to the determination, to establish a corresponding calibration curve for the sulphur-containing starting compound in question. The establishment of a calibration curve is typically conducted by first measuring the electrolysis current for solutions of different concentrations of the sulphur-containing starting compound, i.e. the known compound, used in step a), for example of dimethyl disulphide.

These measurements are then correlated with the concentrations of the dimethyl disulphide in question and reflected in a calibration function for dimethyl disulphide. Subsequently, the electrolysis current is measured by means of pulsed amperometric detection for a sample with an unknown concentration of dimethyl disulphide (for which the corresponding calibration function has been established beforehand). By comparison with the calibration function for dimethyl disulphide, it is possible to use the electrolysis current measured to determine the concentrations for this dialkyl disulphide in the sample in question. Analogously to this procedure, corresponding calibration functions are also established for other sulphur-containing starting compounds. If, in step a) of the process according to the invention, an alkyl mercaptan is used as sulphur-containing starting compound, the expression "sulphur-containing starting compound" in this case encompasses both the alkyl mercaptan and the dialkyl disulphide obtained by a first oxidation of the alkyl mercaptan, which then constitutes the actual sulphur-containing starting compound for the oxidation in step a) of the process according to the invention. In this case, calibration functions are established both for the alkyl mercaptan used initially and for the dialkyl disulphide obtained directly from the oxidation of the alkyl mercaptan.

Preferably, step b) of the process according to the invention therefore comprises the individual steps of
b1) measuring the electrolysis current for a sulphur-containing starting compound by means of pulsed amperometric detection, and
b2) determining the amount and/or the concentration of the sulphur-containing starting compound to be determined by comparison with a calibration function established beforehand for the sulphur-containing starting compound to be determined.

A necessary criterion to allow determination of a sulphur-containing organic compound such as a dialkyl disulphide with the aid of amperometric detection is the presence of at least one free electron pair on the sulphur atom. This is because only compounds having a free electron pair can be adsorbed on electrode surfaces and are therefore electroactive species. In contrast, organic compounds lacking free electron pairs are non-electroactive species. This is because these compounds cannot be adsorbed on electrode surfaces due to the lack of electron pairs and therefore cannot be determined by means of amperometric detection either.

Preferably, therefore, the pulsed amperometric detection is conducted in oxidative mode.

Conducting the pulsed amperometric detection in oxidative mode for determination of sulphur-containing compounds has the advantage that the sulphur-containing starting compound in question, adsorbed at the electrode surface, is oxidized either in one step or in a stepwise manner to a compound that is not electroactive. For example, dimethyl disulphide is oxidized directly to a derivative having at least one oxygen covalently bonded to a sulphur. The end product of this oxidation is a dimethyl sulphone which is hydrolysed in the presence of water to methanesulphonic acid. Another example is methyl mercaptan, which is first oxidized to dimethyl disulphide and then via the above-described oxidation intermediates to dimethyl sulphone, which is finally hydrolysed in the presence of water to methanesulphonic acid. The alkanesulphonic acid present in each case as the end product of the electrolytic oxidation is non-electroactive. This is because the sulphur atom of this compound does not have a free electron pair by which it could be adsorbed at the electrode surface. Therefore, it is also impossible for any adsorbates of alkanesulphonic acid to form at the electrode surface that could either affect the present measurement or later measurements. This advantageously contributes to the accuracy of the process according to the invention. In the context of the present invention, therefore, a pulsed amperometric detection in oxidative mode is in principle also understood to mean a detection in which the alkyl mercaptan, dialkyl disulphide and/or dialkyl polysulphide component adsorbed on the electrode surface is converted either completely or at least virtually completely to oxidized species such as $R^1$—$SO_2$—$SO_2$—$R^1$ where $R^1$ is an alkyl radical.

For the conduction of pulsed amperometric detection, all known different types of carbon and precious metal electrodes are suitable in principle. Typically, for reductive determinations, precious metal electrodes such as gold, silver and gold amalgam electrodes are used, and also mercury film electrodes (see J. Frank, Chimia 1981, 35, 24, P. T. Kissinger, C. S. Brunett, K. Bratin, J. R. Rice, Spec. Publ. (U.S.) 1979, 519, 705 and S. Yao, A. Meyer, G. Henze, Fresenius J. Anal. Chem. 1991, 339, 207).

In the context of the process according to the present invention, however, glassy carbon electrodes have been found not only to be suitable for the determination of dialkyl disulphides, but in fact to be the only type of working electrode which permits reliable determination of dialkyl disulphides. This is indeed surprising since, according to conventional opinion in the literature, carbon electrodes such as glassy carbon electrodes show absolutely no signal for disulphides in the determination of disulphides and thiols, and only do so for thiols (see C. Terashima et al., Analytical Chemistry, Vol. 75 No. 7, Apr. 1, 2003, 1564-1572). Glassy carbon electrodes typically consist of carbon in the form of pins or small rods having a diameter of 2 to 8 mm, which are cemented or compressed into a glass or plastic holder. In comparison to other carbon electrodes such as carbon paste electrodes, glassy carbon electrodes additionally have better chemical durability, since they are stable in solvents such as methanol or acetonitrile. If required, glassy carbon electrodes can be prepared for use by polishing with a diamond paste, followed by immersion in an ultrasonic bath with high purity water.

A further advantage of glassy carbon electrodes is that they allow measurements over a wide range from about −0.8 V to about 1.3 V. In the context of the present invention, it has been shown that, in this wide potential range, the electroactive sulphur-containing compounds, especially dialkyl disulphides and/or dialkyl polysulphides, are oxidized completely or at least virtually completely to non-electroactive species. With the aid of glassy carbon electrodes, therefore, it is possible to conduct the pulsed amperometric detection in oxidative mode.

With regard to the reference electrode, the process according to the present invention is not subject to any restrictions. Therefore, a conceivable combination is that of a glassy carbon electrode as working electrode with any available electrodes of the first kind or second kind as reference electrode. Electrodes of the first kind are understood in the context of the present invention and in accordance with the common knowledge of the person skilled in the art to mean any electrodes whose potential depends directly on the concentration of the surrounding electrolyte solution. These are solid-state electrodes, for example the palladium electrode. In the context of the present invention and in accordance with the common knowledge of the person skilled in the art, electrodes of the second kind are understood to mean those electrodes whose potential depends only indirectly on the surrounding electrolyte solution. By virtue of the specific composition of the electrolyte solution, the potential of the electrode is kept constant. The electrolyte solution consists firstly of a saturated solution of a sparingly soluble salt where the cation consists of the same metal as the electrode and secondly of a readily soluble alkali metal salt of a specific concentration containing the same anion as the sparingly soluble salt. The potential depends on the concentration of the cation of the sparingly soluble salt. The concentration of the cation is in turn coupled via the solubility product of the salt to the concentration of the anion. If the concentration of the anion is kept constant, the potential also therefore remains constant. The anion concentration can be kept virtually constant by selecting a very large value thereof. The actual potential is given by subtraction of the voltage values from the measured value. Important reference electrodes of the second kind are the silver-silver chloride electrode and the calomel electrode. Because of their reliability and problem-free use, the silver-silver chloride reference electrode and palladium reference electrode have been found to be particularly advantageous for the process according to the present invention.

Preferably, therefore, a silver-silver chloride electrode or palladium electrode is used as reference electrode in the pulsed amperometric detection.

In principle, three variants for the performance of a pulsed amperometric detection are feasible.

In the first variant, for the performance of a pulsed amperometric detection, the electrode potential is pulsed to a range in which the analyte is electroactive. The course of the applied potential over time is therefore similar to a step or Heaviside function, except that the graph of the potential curve proceeds continuously, and therefore without interruption, in contrast to the step function. The course of the measurement signal over time features a sudden increase to a maximum value for the electrolysis current and a subsequent immediate decrease in the measured current, which is attributable to the formation of a diffusion layer around the electrode and the continuing growth of this diffusion layer.

In the second variant, for the performance of a pulsed amperometric detection, the electrode potential is briefly pulsed to a range in which the analyte is electroactive. In this case, the course of the potential applied to the working electrode over time features overlaying of the starting potential at periodic intervals for the same duration by identical rectangular potential blocks. The diffusion layer formed at the working electrode between the pulses can be removed by forced or natural convection. The course of the electrolysis current measured over time features a sudden increase and decrease in the electrolysis current, which is associated with the respective pulses in terms of time. Due to the time limit of the higher electrode potential, the decrease in the measured electrolysis current is limited to the duration of the pulse and therefore drops correspondingly lower than in the first variant.

The third variant for the performance of a pulsed amperometric detection comprises a total of three potential profiles: a first potential profile for conditioning the electrode, a second for sorption of the analytes and finally a third potential profile for the electrooxidation of the analyte in question. The electrolysis current is measured only on application of the third potential profile.

It has been shown in the context of the present invention that pulsed amperometric detection with at least three different potential profiles during a complete measurement cycle permits particularly good reproducibility and reliability of the measurement.

Preferably, the pulsed amperometric detection therefore involves at least three potential profiles.

In the context of the present invention, the lowest potential profile (i.e. the most electronegative potential profile) preferably serves for sorption of the analyte at the working electrode and therefore for conditioning of the working electrode. The highest potential profile (i.e. the most electropositive potential profile) in the context of the present invention serves for complete oxidation of adsorbates at the working electrode and therefore results in cleaning of the working electrode. A further potential profile, the height of which is between the lowest and the highest potential profile, in the context of the present invention, serves for electrooxidation of the dialkyl disulphide to be determined, and therefore also serves for measurement of the electrolysis current in question and for determination of the dialkyl disulphide in question.

In the context of the present invention, the sequence of electrooxidation at an oxidation potential, complete oxidation at a cleaning potential and sorption of the analyte at a conditioning potential preferably forms a pulse for a pulsed amperometric detection. Advantageously, an oxidation potential is followed by a cleaning potential. This has the advantage that the compounds incompletely oxidized to non-electroactive species during the electrooxidation or any impurities/residues at the working electrode are completely removed from the working electrode by the application of a more electropositive cleaning potential compared to the oxidation potential and therefore do not impair the subsequent measurement(s). The cleaning potential is preferably followed by a conditioning potential. The application of a conditioning potential facilitates the sorption of the analyte to be determined at the electrode surface. This in turn increases the measurement accuracy of the subsequent measurement of the electrolysis current during the period in which an oxidation potential is applied to the working electrode. With regard to the number of individual specific potential profiles which can be used in a pulsed amperometric detection, the process according to the invention is not subject to any restriction at all.

Preferably, the pulsed amperometric detection therefore includes at least one oxidation potential, at least one cleaning potential and at least one conditioning potential.

Depending on the dialkyl disulphide to be determined, the specific values for the individual potential profiles can be adjusted such that, during the period in which the respective potential profiles of oxidation potential, cleaning potential and conditioning potential are applied to the working electrode, only the effects ascribed to the individual potential profile occur.

It has been shown in the context of the present invention that an electrooxidation at an oxidation potential in the range from about +0.5V to about +1.3V is suitable for the determination of all common dialkyl disulphides, and in particular for the determination of dimethyl disulphide, which is an intermediate in the production of commercially important methanesulphonic acid. It has further been shown that a cleaning potential in the region of at least about +1.5 V is sufficient to ensure complete cleaning of the working electrode to remove adsorbates or remaining contaminants. For conditioning the working electrode, a conditioning potential in the range of about −0.5V to about +0.5V has also been found to be suitable in order to facilitate the sorption of the analyte for the subsequent electrooxidation. In the context of the present invention, the word "about" in connection with the statement of potential values refers to a deviation of +1-10% from the value explicitly stated.

Preferably, therefore, the oxidation potential in the pulsed amperometric detection of a sulphur-containing starting compound in step b) of the process according to the invention has a value of about +0.5 V to about +1.3 V, the cleaning potential has a value of at least about +1.5 V and the conditioning potential has a value of about −0.5 V to about +0.5 V.

For the determination of dialkyl disulphides in alkanesulphonic acids, particularly for the determination of dimethyl disulphide in methanesulphonic acid, an oxidation potential at a value of about +0.8 V to about 1.2 V, a cleaning potential at a value of at least about +1.5 V and a conditioning potential at a value of about −0.3 V to about +0.3 V have been found to be particularly suitable for assuring accurate and reproducible results.

More particularly, therefore, the oxidation potential in the pulsed amperometric detection of a sulphur-containing starting compound in step b) of the process to the invention has a value of about +0.8 V to about 1.2 V, the cleaning potential has a value of at least about +1.5 V and the conditioning potential has a value of about −0.3 V to about +0.3 V.

The applying of these and aforementioned potential profiles to the working electrode is not subject to any restrictions. For example, a specific potential having a constant value from the abovementioned ranges for the potential in question can be applied to the working electrode over the entire period in which the electrode potential in question is being applied. A ramp profile for the potential in question is also feasible: In this case, the value of the potential in question on the working electrode at the beginning of the period is well below its maximum value, having the minimum value thereof in the borderline case, and by the end of the period its value will increase with a constant potential rise per defined unit time, in the borderline case to its maximum value.

In order to ensure that the purposes of applying the respective potential profiles to the working electrode are indeed accomplished, the potentials in question have to be applied to the working electrode for a sufficient period. Irrespective of the dialkyl disulphide to be determined, the following periods of time have been found to be favourable for the effects ascribed to the potential profiles of oxidation potential, cleaning potential and conditioning potential to indeed occur: at least about 60 ms for the oxidation potential, at least about 10 ms for the cleaning potential and at least about 40 ms for the conditioning potential. In the context of the present invention, the word "about" in connection with the statement of time intervals refers to a deviation of +1-10% from the value explicitly stated. Deviations of this order of magnitude generally do not lead to a notable deterioration of the signal-to-noise ratio.

Preferably, therefore, the duration of the oxidation potential in the pulsed amperometric detection of a sulphur-containing starting compound in step b) of the process according to the invention is at least about 60 ms, the duration of the cleaning potential at least about 10 ms, and the duration of the conditioning potential at least about 40 ms.

Even though the corresponding electrolysis current for the dialkyl disulphide in question flows in principle within the period in which the oxidation potential is applied to the working electrode, the electrolysis current is nevertheless not measured for the entire period. This is because the electrolysis current is not yet constant at the start of the duration of the oxidation potential. In order to avoid measurement inaccuracies resulting from fluctuations in the electrolysis current, the electrolysis current is therefore not measured until after it has settled at a constant value. The electrolysis current is typically measured only in the latter half of the duration of the oxidation potential, preferably only in the last third of the duration of the oxidation potential.

The electrolysis current as such constitutes a brief signal for which the signal-to-noise ratio is of relevance for maximum accuracy of measurement thereof. For the measurements of brief amperometric signals, the signal-to-noise ratio is influenced by the instrumental procedure used for sampling of the electrode current. A significant noise component of the amperometric determination at constant electrode potential, i.e. without pulsing the working electrode potential, is sinusoidal and correlates with the 60 Hz line frequency. In order to achieve measurements of maximum accuracy with the aid of pulsed amperometric detection, therefore, in the context of the present invention, a signal corresponding on average to a multiple of the period of an individual 60 Hz oscillation, i.e. an oscillation period of 16.7 ms, is used. In this case, there is therefore no contribution of the sinusoidal 60 Hz noise signal to the signal strength. The time integral of a sinusoidal 60 Hz noise signal has the value of 0 for every integer multiple v of the periods having an oscillation time of 16.7 ms. The analytical signal strength can therefore be considerably increased for multiples v of the oscillation period which are significantly greater than 1. Therefore, if the analytical signal during the entire period of v*16.7 ms has a constant value, then the signal-to-noise ratio is enhanced by the factor v. In the context of the present invention, integer multiples v of the oscillation time of 16.7 ms of at least 6 have been found to be favourable in order to ensure precise and reproducible results for the electrolysis current measured in the latter half, preferably in the last third, of the duration of the oxidation potential.

Preferably, therefore, the measurement duration in the pulsed amperometric detection of a sulphur-containing starting compound in step b) of the process according to the invention is an integer multiple of 16.7 ms.

At a duration of at least 300 ms for the oxidation potential, the measurement duration for the electrolysis current is between about 100 ms and 150 ms. The measurement period in that case is preferably about 50 ms, about 67 ms, about 84 ms, about 100 ms, about 117 ms, about 134 ms and about 150 ms. These cases are 3 times, 4 times, 5 times, 6 times, 7 times, 8 times or 9 times the oscillation period of 16.7 ms.

Preferably, therefore, the duration of the oxidation potential in the pulsed amperometric detection of a sulphur-containing starting compound in step b) of the process according to the invention is at least about 300 ms.

In the case of a duration of the oxidation potential of at least about 300 ms, the duration of the cleaning potential is preferably at least about 50 ms and the duration of the conditioning potential preferably at least about 200 ms.

A typical duration of a measurement cycle composed of oxidation potential, cleaning potential and conditioning potential therefore has a total duration of at least about 500 ms.

The electrolysis current is typically measured only in the latter half of the duration of the oxidation potential, preferably only in the last third of the duration of the oxidation potential. Therefore, the duration of measurement thereof is preferably an integer multiple of 16.7 ms and especially between half and one third of the duration of the oxidation potential.

In order to have sufficient knowledge about the progress of the oxidation of the sulphur-containing starting compounds to the corresponding alkanesulphonic acid and any amount of additional oxidizing agent required to complete the oxidation reaction, it is also necessary to determine the sulphur-containing starting compound in the reaction output from step a). Typically, a dialkyl disulphide and/or a dialkyl polysulphide is used as sulphur-containing starting compound for preparation of alkanesulphonic acids. The dialkyl disulphides are then prepared in a reaction preceding step a), for example in a base-catalysed oxidation of alkyl mercaptans with sulphur to release hydrogen sulphide, followed by a purification of the crude dialkyl disulphides, preferably by a distillation. This has the advantage that an at least essentially pure sulphur-containing starting compound is supplied to the oxidation of step a). In this way, the formation of possible by-products is avoided and, at the same time, the amount of oxidation intermediates formed remains manageable.

In a further embodiment of the process according to the invention, therefore, in step b), a dialkyl disulphide and/or a dialkyl polysulphide is determined as sulphur-containing starting compound.

As already explained, dialkyl disulphides or dialkyl polysulphides can be determined with the aid of amperometry since they have free electron pairs on sulphur atoms, on account of which they can be absorbed at electrode surfaces, in order to be electrochemically oxidized there. However, some of the oxidation intermediates that occur in the oxidation of dialkyl disulphides or dialkyl polysulphides, especially S-alkyl alkanesulphonates, also have free electron pairs on at least one of the sulphur atoms. Consequently, these oxidation intermediates can also be sorbed at the working electrode and electrochemically oxidized there. However, this would affect the measurement of the electrolysis current in the pulsed amperometric determination of the sulphur-containing starting compound and lead to higher values for the dialkyl disulphide or dialkyl polysulphide to be determined. This is problematic especially when the UV-vis determination of oxidation intermediates, especially of S-alkyl alkanesulphonates, is downstream of the pulsed amperometric determination of dialkyl disulphides or dialkyl polysulphides. This is because, in that case, no S-alkyl alkanesulphonate would be determined in the reaction output from step a) even if they were actually present therein. As a consequence, the S-alkyl alkanesulphonates in the most unfavourable case could get into the distillation apparatuses downstream of the production and lead to elemental sulphur precipitates therein and hence to disrupted operation.

The performance of the process according to the invention can be significantly increased by first taking a sample from the reaction output from step a) and dividing this sample into two separate samples. Subsequently, the determination of oxidation intermediates, especially S-alkyl alkanesulphonates, is undertaken, preferably by means of UV-vis spectroscopy from one separate sample, and the determination of sulphur-containing starting compounds, especially dialkyl disulphides and/or dialkyl polysulphides, preferably by means of amperometric detection, from the other separate sample.

In one embodiment of the process according to the invention, therefore, the determination of oxidation intermediates and the determination of sulphur-containing starting compounds are effected independently in separate samples from the reaction output from step a).

Alternatively, both the accuracy and reliability in the determination of sulphur-containing starting compounds, especially of dialkyl disulphides and dialkyl polysulphides, in the presence of oxidation intermediates from step a) can be improved by subjecting the sample from the reaction output from step a) to a chromatographic separation prior to the determination in step b). The sulphur-containing starting compounds, especially dialkyl disulphides and dialkyl polysulphides, are much less polar than the oxidation intermediates, especially S-alkyl alkanesulphonates. Therefore, the sulphur-containing starting compounds and oxidation intermediates differ in their respective retention characteristics in a chromatographic separation. For this reason, sulphur-containing starting compounds are eluted from the separation column after different retention times than the oxidation intermediates. This has the advantage that the compounds to be determined enter the measurement cell for the pulsed amperometric detection at different times and thus do not affect one another in the individual determinations, which leads especially to an improvement in the accuracy and reliability in the determination of dialkyl disulphides and/or dialkyl polysulphides with the aid of pulsed amperometric detection.

Moreover, chromatographic separation of a sample from the reaction output from step a) of the process according to the invention preceding the determination of sulphur-containing starting compounds and/or of oxidation intermediates in step b) of the process according to the invention also permits the establishment of separate samples each containing different compounds from the sample from the reaction output from step a). Preferably, a first sample contains only one sulphur-containing starting compound, for example a dialkyl disulphide and/or dialkyl polysulphide, and another sample contains only one oxidation intermediate, for example an S-alkyl alkanesulphonate.

In one embodiment, the process according to the invention therefore additionally comprises the step, upstream of step b), of chromatographic separation of a sample from the reaction output from step a).

In the context of the present invention, reversed phase chromatography has been found to be a suitable method for separation of sulphur-containing starting compounds, especially dialkyl disulphides and/or dialkyl polysulphides, and oxidation intermediates, especially S-alkyl alkanesulphonates. In the case of use of reversed phase chromatography with a UV-vis spectrometer, for example, S-methyl methanesulphonate is detected after only 5.6 minutes, while dimethyl disulphide is not detected until after 36.6 minutes. The difference between the retention times of dialkyl disulphides or dialkyl polysulphides and of S-alkyl alkanesulphonates is thus large enough to be able to separate these compounds efficiently from one another. This enables reliable and precise determination of dialkyl disulphides or dialkyl polysulphides and S-alkyl alkanesulphonates.

Preferably, therefore, the chromatographic separation is performed in the form of reversed phase chromatography.

With regard to the configuration of the performance of this reversed phase chromatography, the process according to the present invention is not subject to any restrictions in principle. Therefore, all feasible configurations of reversed phase chromatography, such as ion chromatography and high-performance liquid chromatography, are usable in principle in the process according to the present invention. In the context of the present invention, however, ion chromatography has been found to be particularly suitable since it permits, with a manageable level of complexity, complete separation of the sample from the reaction output from step a) of the process according to the invention into its individual components. Moreover, ion chromatography has the advantage over high-performance chromatography that it permits a greater number of options for adjustment of the parameters for (as far as possible) optimal separating conditions.

Particular preference is therefore given to conducting the chromatographic separation as ion chromatography.

Polar solvents suitable for performance of the reversed phase chromatography for sulphur-containing starting compounds, especially dialkyl disulphides and/or dialkyl polysulphides, and oxidation intermediates, especially S-alkyl alkanesulphonates, are protic solvents such as methanol, ethanol and water, or mixtures of protic solvents. In the context of the present invention, the term "protic solvent" is used in accordance with the common knowledge of the person skilled in the art and therefore refers to those compounds having a functional group in the molecule from which hydrogen atoms can be detached as protons, either without the action of bases or by the action of weak bases. In the context of the present invention, a mixture of methanol and water has proven to be particularly suitable for the performance of the chromatographic separation.

Preferably, the process according to the invention therefore additionally comprises the step, preceding the determination in step b), of dissolving a sample from the reaction output from step a) in a protic solvent or a mixture of protic solvents, especially in a mixture of methanol and water.

For very substantial separation, a suitable mobile phase in the context of the present invention has been found to be one based on a mixture of 70% by volume+/−10% by volume of water with 30% by volume+/−10% by volume of methanol.

More preferably, the process according to the invention therefore additionally comprises the step, preceding the determination in step b), of dissolving a sample from the reaction output from step a) in a mixture of methanol and water in a volume ratio of methanol to water of 2:8 to 4:8.

Preferably, by dissolving a sample from the reaction output from step a) in a protic solvent or a mixture of protic solvents, the sample is also diluted by a factor of 10 to 1000.

The eluent used for the chromatographic separation flows with the sample through the amperometric measurement cell after exit from the chromatography column. Therefore, the protic solvent or the mixture of protic solvents used for dissolution of the sample must fulfil not only the function of an eluent in the chromatographic separation but also that of an electrolyte in the subsequent determination of the dialkyl disulphide by means of pulsed amperometric detection. This requires intrinsic conductivity of the solvent or solvent mixture in question, which is generally not achieved solely by any ions such as chloride, nitrate or the like that are additionally present in the sample. In the simplest case, the required conductivity is caused by the alkanesulphonic acid, preferably methanesulphonic acid, present in the sample.

Essentially, the process according to the invention is not subject to any restrictions with regard to the oxidizing agent, provided that it is assured that the oxidizing agent is capable of converting a sulphur-containing starting compound and the oxidation intermediates that result from the oxidation of the sulphur-containing starting compound to the desired alkanesulphonic acids. A suitable oxidizing agent in the process according to the invention is oxygen, either in free form or in bound form. In the context of the present invention, the term "oxygen in free form" is used in accordance with the common knowledge of the person skilled in the art and refers to oxygen which is not part of an organic or inorganic compound by virtue of covalent bond(s). Oxygen in free form is, for example, molecular oxygen $O_2$, ozone $O_3$ or an oxygen radical. According to this understanding, therefore, an oxygen molecule or an oxygen radical which is part of a complex or is present in coordinated form is also to be understood as oxygen in free form. Oxygen in free form used in the process according to the invention may therefore be, inter alia, pure oxygen or an oxygen-enriched gas stream, for example oxygen-enriched air or a mixture of pure oxygen and a so-called inert gas which is unreactive under the oxidation conditions, for example nitrogen or argon. By contrast, the term "oxygen in bound form" refers to any oxygen which is part of an inorganic or organic compound by virtue of at least one covalent bond. Ultimately, the compounds having oxygen in bound form serve to transfer oxygen atoms to the sulphur atoms present in the dialkyl disulphide, in order to oxidize them from the formal oxidation state of −1 in the dialkyl disulphide (stepwise) up to the oxidation state of +3 in the dialkyl disulphone. Alternatively, in the context of the present invention, it is also possible to simultaneously use oxygen in free form and oxygen in bound form for oxidation of a sulphur-containing starting compound, especially for oxidation of the dialkyl disulphide and/or dialkyl polysulphide.

In one embodiment of the process according to the invention, therefore, step a) is conducted with free oxygen and/or with oxygen in bound form.

Preference is given to conducting the process according to the invention in the presence of catalytic amounts of nitric acid. The expression "catalytic amounts of nitric acid" refers in the context of the present invention to all amounts of nitric acid that are smaller than the stoichiometric amount of nitric acid required for oxidation of a sulphur-containing compound used in accordance with the invention. More particularly, the expression "catalytic amounts of nitric acid" refers to a ratio of sulphur-containing starting compound, preferably dialkyl disulphide, to nitric acid of 2000:1 (mol/mol) to 1:1 (mol/mol), where this ratio includes all values that can be expressed by whole and real numbers from 2000:1 (mol/mol) to 1:1 (mol/mol) inclusive. This ratio encompasses especially the values of 2000:1 (mol/mol), 1000:1 (mol/mol), 500:1 (mol/mol), 200:1 (mol/mol), 100:1 (mol/mol), 90:1 (mol/mol), 80:1 (mol/mol), 70:1 (mol/mol), 60:1 (mol/mol), 50:1 (mol/mol), 40:1 (mol/mol), 30:1 (mol/mol), 20:1 (mol/mol), 10:1 (mol/mol), 5:1 (mol/mol), 2:1 (mol/mol) and 1:1 (mol/mol). In the context of the present invention, these values relate to the concentrations of the components in question in the reaction mixture at the start of the reaction.

Preferably, in the process according to the invention, for oxidation, air, a gas stream enriched with oxygen in free form and/or pure oxygen is fed in in free form, particular preference being given to the use of oxygen in free form and/or a gas stream enriched with oxygen in free form for oxidation. This is because the molecular oxygen and the water present in the reaction mixture regenerate nitrogen oxides which have formed both through the oxidation reaction and through thermal breakdown back to nitric acid. In the case of performance of the process according to the invention with nitric acid as oxidizing agent and/or as catalyst, this regeneration automatically always takes place as a side reaction. This has the advantage that continuous addition of nitric acid in the process according to the invention is preferably not required.

If, however, the nitrogen oxides are not fully regenerated to nitric acid, and there should be a resultant loss of nitric acid, this loss can be compensated for by addition of fresh nitric acid. This supplementation of non-regenerated and hence lost nitric acid can be effected either sporadically or continuously depending on the amounts of fresh nitric acid required in each case.

The oxidation of sulphur-containing starting compounds, especially of dialkyl disulphide and/or dialkyl polysulphide, with the aid of a gas stream enriched with oxygen in free form has the advantage that a gas stream which is relatively favourable compared to pure oxygen is fed into the reaction. In addition, in accordance with the course of the oxidation reaction, the oxygen content in the gas stream to be fed in can be adjusted as desired. In the simplest case, this gas stream is air with more than 20.9% by volume (percent by volume) of oxygen in free form.

Feeding a gas stream with at least 21% by volume of oxygen in free form into the reaction mixture ensures that both very substantial oxidation of the dialkyl disulphide to the corresponding alkanesulphonic acid and regeneration of the nitrogen oxides $NO_x$ to nitric acid is achieved.

Preference is therefore given, for oxidation, to feeding a gas stream containing oxygen in free form and having a content of at least 21% by volume of oxygen in free form, especially more than 21% by volume of oxygen in free form.

In the context of the present invention, the expression "at least 21% by volume of oxygen in free form" refers to all values of greater than or equal to 21% by volume up to and including 100% by volume that can be expressed by whole and real numbers. In the borderline case, the gas stream having a content of at least 21% by volume of oxygen in free form is pure oxygen in free form, preferably molecular oxygen $O_2$.

With regard to the number of reactors in which the oxidation is conducted in step a) of the process according to the invention, the process according to the invention is not subject to any restrictions in principle. In the case of use of two or more reactors in the process according to the invention, the reactors may be arranged either in parallel or in series. Also conceivable is a mixture of reactors arranged in parallel and series.

In one embodiment of the process according to the invention, therefore, step a) is conducted in at least one reactor.

If step a) of the process according to the invention takes place only in a single reactor, the amount of additional oxidizing agent for conversion of the sulphur-containing starting compounds and/or oxidation intermediates determined in step b) is also fed into this reactor in step c). However, this process regime cannot prevent the oxidation of the sulphur-containing starting compounds to the desired alkanesulphonic acid from not always proceeding to completion, even when the oxidizing agent required for oxidation is fed into the reactor in a stoichiometrically sufficient amount. If, for example, there is a variation in the concentration of the sulphur-containing starting compound in the feed stream, it may be the case that the amount of the oxidizing agent fed into the reactor is insufficient to assure full oxidation of the starting compounds to the alkanesulphonic acid. Moreover, the residence time of the reactants in the reactor may be too short or the starting compounds and the oxidizing agent may not have been mixed sufficiently to achieve complete oxidation of the starting compounds.

Preferably, step a) of the process according to the invention is therefore conducted in two reactors arranged in series, with the reaction output from the oxidation conducted in the first reactor being fed into the second reactor and optionally into further reactors. Depending on the degree of conversion of the sulphur-containing starting compounds for the oxidation reaction conducted in the first reactor, step a) of the process according to the invention can be conducted in all reactors of a series of reactors. This has the advantage that essentially full conversion of the sulphur-containing starting compounds to the desired alkanesulphonic acids is achieved. This avoids accumulation of unconverted sulphur-containing starting compounds and/or oxidation states in the reaction mixture.

In a preferred embodiment of the process according to the invention, therefore, step a) is conducted in at least two reactors arranged in series.

In the context of the process according to the invention, the performance of step a) in at least two reactors arranged in series encompasses either one row of reactors arranged in series or two or more rows of reactors arranged in series, in which case the two or more rows are arranged parallel to one another.

In the case of performance of the process according to the invention in at least two reactors arranged in series, the process according to the invention is conducted in a combination of a main reactor with a postreactor. The postreactor serves to complete the oxidation reaction and is therefore also referred to as finisher reactor. For example, it is possible to combine a continuously operated stirred tank reactor as main reactor, in which the majority of the sulphur-containing starting compounds, especially the dialkyl disulphide and/or dialkyl polysulphide, is converted, with a flow tube as postreactor for completion of the reaction.

In order to ensure that the oxidizing agent is being fed into the second reactor and optionally into further reactors in the amount required for completion of the oxidation reaction, step b) of the process according to the invention has to be effected downstream of the reactor which precedes that reactor to which the reaction output is supplied and into which the additional oxidizing agent is fed. Alternatively, the additional oxidizing agent can also be fed into each of the reactors arranged in series.

In a preferred embodiment of the process according to the invention, therefore, step b) and, if required, step c) is conducted downstream of the first reactor and, in the case of more than two reactors arranged in series, also downstream of the second and every further reactor.

With regard to the choice of additional oxidizing agent, the process according to the invention is not subject to any restrictions. It is possible to use exclusively free oxygen or oxygen in bound form, as defined above, as oxidizing agent in the overall process. Alternatively, it is also possible to use free oxygen and oxygen in bound form, each in different amounts, in different steps of the process according to the invention. Compared to oxygen in bound form, for example as nitric acid, the use of free oxygen as oxidizing agent has the advantage that an inexpensive oxidizing agent is being used. The advantage of oxygen in bound form, by contrast, is that it generally has a higher oxidation potential than free oxygen. By the choice of oxygen-containing oxidizing agents suitable for the respective process steps, it is possible to optimally utilize the respective advantages of the oxidizing agents in question. The use of free oxygen as oxidizing agent is advantageous particularly when the aim is to oxidize large amounts of sulphur-containing starting compounds. This is typically the case when step a) is performed in the first of at least two reactors. The use of oxygen in bound form as oxidizing agent, preferably nitric acid, is appropriately effected when the oxidation reaction has to be concluded. This is typically the case when, in step c) of the process according to the invention, additional oxidizing agent is fed into the second or every further reactor of a series of reactors for performance of step a), or when step a) is conducted in just one reactor.

In a further preferred embodiment of the process according to the invention, therefore, the oxidation in the first reactor is conducted with free oxygen and, in the case of more than two reactors arranged in series, if required, oxygen in bound form is fed into the second and every further reactor.

In the context of the present invention, it has been found that UV-vis spectroscopy and pulsed amperometric detection, both alone and in combination with one another, are suitable for controlling the preparation of alkanesulphonic acid by oxidation of sulphur-containing starting compounds. Through the inventive use of UV-vis spectroscopy and/or pulsed amperometric detection, in accordance with the invention, both unconverted sulphur-containing starting compounds and/or oxidation intermediates which can lead to precipitates of elemental sulphur and associated blockages of pipelines and column heads are determined. On the basis of this determination, it is possible to supply the amount of additional oxidizing agent required to complete the oxidation reaction into the reactor(s) in question. The performance of the oxidation of sulphur-containing starting compounds, irrespective of the specific configuration of the process regime, can be controlled in a crucial manner with the aid of use of UV-vis spectroscopy and/or pulsed amperometric detection.

The present invention therefore also further provides for the use of UV-vis spectroscopy and/or pulsed amperometric detection in the preparation of alkanesulphonic acids.

In one embodiment of the use according to the invention, alkanesulphonic acids are prepared by oxidation of sulphur-containing starting compounds, wherein the sulphur-containing starting compounds are selected from the group consisting of alkyl mercaptan, dialkyl disulphide and dialkyl polysulphide having three to nine sulphur atoms.

In a preferred embodiment of the use according to the invention, alkanesulphonic acids are prepared by oxidizing methyl mercaptan, dimethyl disulphide and/or dimethyl polysulphide having three to nine sulphur atoms.

The concept of the invention, that of controlling the performance of the oxidation of an organic compound to the desired target compound by the determination of unreacted or not completely reacted starting compounds and oxidation intermediates, is not restricted to the oxidation of sulphur-containing starting compounds to the corresponding alkanesulphonic acids. Instead, this concept can also be applied to the performance of other oxidation reactions.

The present invention therefore also further provides an apparatus for performance of oxidation reactions, comprising i) at least one reactor for oxidizing at least one starting compound,
ii) at least one measuring unit, downstream of the reactor, for determining nonoxidized starting compounds and/or oxidation intermediates from the oxidation of the starting compound to the desired target compound in the reaction output from step a), and
iii) a unit, in contact with the at least one measuring unit, for supplying additional oxidizing agent to the at least one reactor.

The same aspects apply to the arrangement of components i) to iii) of the apparatus according to the invention and the mode of operation of these components as to the arrangement and mode of operation of the corresponding components in the process according to the invention, especially with regard to the number and arrangement of the reactors and the determination of nonoxidized starting compounds and/or oxidation intermediates from the oxidation of the starting compound to the desired target compound and the supply of additional oxidizing agent.

Accordingly, the apparatus according to the present invention is in particular an apparatus for carrying out the oxidation of a sulfur containing starting compound, such as an alkylmercaptan, dialkyldisulfide, dialkylpolysulfide to the corresponding alkanesulfonic acid.

In one embodiment, the apparatus according to the invention therefore has at least two reactors arranged in series.

In a further embodiment, the apparatus according to the invention has measurement units for determination of nonoxidized starting compounds and/or nonoxidized oxidation intermediates downstream of the first reactor and, in the case of more than two reactors arranged in series, also downstream of the second and every further reactor.

With regard to the measurement unit for determination of unconverted starting compounds and/or oxidation intermediates, the apparatus according to the invention is not subject to any restrictions. Instead, it is possible in principle to use all measurement units which permit reliable determination of unconverted starting compounds and/or oxidation intermediates within a minimum time interval, in order that additional oxidizing agent can be supplied to the at least one reactor for completion of the oxidation reaction without a significant time delay, preferably within a few seconds after the determination. With this precondition, the UV-vis spectrometer and the pulsed amperometric detector have been found to be measurement units suitable for the apparatus according to the invention. This is because, with UV-vis spectrometers and pulsed amperometric detectors, unconverted starting compounds and/or oxidation intermediates in the reaction output from oxidation reactions can be determined reliably and with high accuracy within a short time and without any great apparatus complexity. Whether just one UV-vis spectrometer, just one pulsed amperometric detector or a combination thereof is used for the determination follows from the respective suitability of the starting compounds in question and the oxidation intermediates in the oxidation for the respective methods of determination.

In one embodiment of the apparatus according to the invention, the measurement unit is therefore a UV-vis spectrometer and/or an amperometric detector, preferably a pulsed amperometric detector.

In a preferred embodiment, the apparatus according to the invention has a UV-vis spectrometer and an amperometric detector downstream of the first reactor and, in the case of more than two reactors arranged in series, also downstream of the second and every further reactor.

In an additional embodiment, the apparatus according to the invention has a unit for feeding of free oxygen into the first reactor, in order to be able to conduct the oxidation reaction in the first reactor, and in the case of more than two reactors arranged in series also units for feeding oxygen in bound form into the second or every further reactor, in order to complete the oxidation reaction to give the desired oxidation product.

The examples which follow demonstrate the suitability of pulsed amperometric detection for determination of oxidation intermediates, especially of S-alkyl alkanesulphonates such as S-methyl methanesulphonate, in a matrix containing alkanesulphonic acid, especially methanesulphonic acid.

FIGURES

FIG. 1: Chromatogram of Comparative Example 1
FIG. 2: Chromatogram of Comparative Example 2
FIG. 3: Chromatogram of Comparative Example 3
FIG. 4: Chromatogram of Comparative Example 4
FIG. 5: Chromatogram of Example 1
FIG. 6: Chromatogram of Example 2
FIG. 7: Chromatogram of Example 3
FIG. 8: Chromatogram of Example 4
FIG. 9: $^1$H NMR spectrum of Comparative Experiment 5

EXAMPLES

I. Technical Equipment
1. Equipment Used:

Professional Sample Processor 858 (No. 2.858.0010 from Metrohm) sample handling device equipped with an 800 Dosino 800 (No. 2.800.0010 from Metrohm) metering system.

882 Compact IC plus (No. 2.850.9110 from Metrohm) ion chromatograph equipped with a Vario 944 (No. 2.944.0010 from Metrohm) UV/VIS detector, an IC Amperometric Detector (No. 2.850.9110 from Metrohm) and a pressure gauge.

883 Basic IC plus (2.883.0020 from Metrohm) ion chromatograph equipped with a conductivity detector in the form of the module iDetector (standard equipment of the 883 Basic IC plus ion chromatograph) and a pressure gauge.

In the experiments, the first device is the sample handling system, followed by the ion chromatograph which is equipped with a relevant detector.
2. Chromatography Columns:

In the 882 Compact IC plus ion chromatograph, a column of the type Phenomenex Gemini 5U C6-Phenyl 110A 250/4.6 is used. Alternatively, a column of the type ProntoSil 120-5-C18 AQ 150/4.0 (6.1008.100 from Metrohm) may also be used.

In the 883 Basic IC Plus ion chromatograph, a Metrosep A Supp 1 Guard/4.6 was used as pre-column or guard column and an anion separating column Metrosep A Supp 5 250/4.0 as main column. A Metrohm Suppressor-Module MSM was also used as cation exchanger.
3. Eluents:

Chemicals used:
ultrapure water having a conductivity resistance of 18.2 MOhm and a TOC of 5 ppb, where TOC stands for total organic carbon and states the sum of the whole organic carbon in a water sample (from a Milli-Q Advantage A10 ultrapure water system with Q-POC dispenser or a Millipore system),
LiChrosolv HPLC Grade (high performance liquid chromatography) methanol (1.06007 from Merck),
potassium dihydrogenphosphate 99% (1.04873 from Merck),
phosphoric acid 85% (1.00573 from Merck), and
methanesulphonic acid (471356 from Sigma Aldrich).

The eluent for the 882 Compact IC plus ion chromatograph was composed of:
70% ultrapure water,
30% methanol,
10% potassium dihydrogenphosphate, and
1.2 g of phosphoric acid.

The eluent for the 883 Basic IC plus ion chromatograph was composed of:
100% ultrapure water,
3.2 mmol of sodium carbonate, and
1.0 mmol of dihydrogencarbonate.

II. Amperometric Detection at Constant Voltage

For comparison with pulsed amperometric detection, dimethyl disulphide (DMDS) in a sample from the preparation of methanesulphonic acid (MA) by oxidation of dimethyl disulphide was determined by means of amperometric detection at constant voltage: An analyte was used, which was provided by dissolving 2 drops of the sample from the methanesulphonic acid preparation in 50 ml of a mixture of acetonitrile and water (ratio by volume 30:70) (referred to as analyte V below). The measurements were conducted over a period of about one hour using a 882 Compact IC Plus 1 ion chromatograph (2.850.9110 from Metrohm), which was equipped with a ProntoSil 120-5-C18 AQ—150/4.0 separating column (6.1008.100 from Metrohm), a Metrosep RP2 Guard/3.5 (6.1011.030 from Metrohm) and an amperometric detector (2.850.9110 from Metrohm). This detector has a measurement cell of the wall jet cell type (6.5337.020 from Metrohm), equipped with a glassy carbon working electrode (6.1257.220 from Metrohm) of diameter 3 mm, a silver/silver chloride reference electrode (6.1257.720 from Metrohm) and an auxiliary electrode (6.1247.000 from Metrohm). The injection volume was 20 µl and the temperature of the separating column was about 25° C.

Thereafter, the determinations of dimethyl disulphide were compared with one another in order to be able to make conclusions as to the reproducibility and reliability of the amperometric determination at constant voltage. For this purpose, the values for the area under the peak for dimethyl disulphide in the relevant chromatograms were compared with one another.

Comparative Example 1

At time t=0 min, the analyte V was injected into the ion chromatograph. The parameters for the ion chromatography conducted were:
Eluent: MeOH:H$_2$O (3:7)+2 g/l KH$_2$PO$_4$+2 g/l H$_3$PO$_4$
Flow rate: 1.2 ml/min
Pressure: 173.1 bar
Recording duration: 20.7 min The components determined in the eluate of this ion chromatography are listed in table 1 and the chromatogram of this determination is shown in FIG. 1. The numbers of the peaks in this table correspond to the correspondingly numbered peaks in the chromatogram of FIG. 1.

TABLE 1

Results of the determination in Comparative Example 1

| Peak No. | Retention time [min] | Area (nA) * min | Height [nA] | Component |
|---|---|---|---|---|
| 1 | 2.997 | 0.0253 | 0.176 | Bromide |
| 2 | 3.457 | 0.0163 | 0.148 | Nitrate |
| 3 | 4.415 | 0.4227 | 3.483 | Phosphate |
| 4 | 15.835 | 352.7363 | 958.275 | DMDS |

Comparative Example 2

At time t=22 min, the analyte V was injected into the ion chromatograph. The parameters for the ion chromatography conducted were:
Eluent: MeOH:$H_2O$ (3:7)+2 g/l $KH_2PO_4$+2 g/l $H_3PO_4$
Flow rate: 1.2 ml/min
Pressure: 170.8 bar
Recording duration: 18.5 min The components determined in the eluate of this ion chromatography are listed in table 2 and the chromatogram of this determination is shown in FIG. 2. The numbers of the peaks in this table correspond to the correspondingly numbered peaks in the chromatogram of FIG. 2.

TABLE 2

Results of the determination in Comparative Example 2

| Peak No. | Retention time [min] | Area (nA) * min | Height [nA] | Component |
|---|---|---|---|---|
| 1 | 2.988 | 0.0230 | 0.163 | Bromide |
| 2 | 3.455 | 0.0140 | 0.149 | Nitrate |
| 3 | 4.405 | 0.3272 | 2.717 | Phosphate |
| 4 | 15.752 | 321.3513 | 891.404 | DMDS |

When an identical analyte was used, by amperometric determination at constant voltage, only 22 minutes after the first measurement (Comparative Example 1), an area value 8.9% lower is obtained for the determination of dimethyl disulphide in methanesulphonic acid.

Comparative Example 3

At time t=42 min, the analyte V was injected into the ion chromatograph. The parameters for the ion chromatography conducted were:
Eluent: MeOH:$H_2O$ (3:7)+2 g/l $KH_2PO_4$+2 g/l $H_3PO_4$
Flow rate: 1.2 ml/min
Pressure: 173.1 bar
Recording duration: 20.7 min The components determined in the eluate of this ion chromatography are listed in table 3 and the chromatogram of this determination is shown in FIG. 3. The numbers of the peaks in this table correspond to the correspondingly numbered peaks in the chromatogram of FIG. 3.

TABLE 3

Results of the determination in Comparative Example 3

| Peak No. | Retention time [min] | Area (nA) * min | Height [nA] | Component |
|---|---|---|---|---|
| 1 | 1.908 | 0.0337 | 0.175 | MSA |
| 2 | 2.992 | 0.0234 | 0.175 | Bromide |
| 3 | 3.458 | 0.0148 | 0.154 | Nitrate |
| 4 | 4.403 | 0.2953 | 2.442 | Phosphate |
| 5 | 6.002 | 0.0066 | 0.030 | MMTS |
| 6 | 15.705 | 303.7108 | 853.682 | DMDS |

Only 42 minutes after the first measurement (Comparative Example 1), by means of amperometric determination at constant voltage, an area value 13.9% lower was obtained for dimethyl disulphide.

Comparative Example 4

At time t=62 min, the analyte V was injected into the ion chromatograph. The parameters for the ion chromatography conducted were:
Eluent: MeOH:$H_2O$ (3:7)+2 g/l $KH_2PO_4$+2 g/l $H_3PO_4$
Flow rate: 1.2 ml/min
Pressure: 168.0 bar
Recording duration: 25.0 min The components determined in the eluate of this ion chromatography are listed in table 4 and the chromatogram of this determination is shown in FIG. 4. The numbers of the peaks in this table correspond to the correspondingly numbered peaks in the chromatogram of FIG. 4.

TABLE 4

Results of the determination in Comparative Example 4

| Peak No. | Retention time [min] | Area (nA) * min | Height [nA] | Component |
|---|---|---|---|---|
| 1 | 2.720 | 0.0037 | 0.059 | Nitrite |
| 2 | 3.000 | 0.0232 | 0.150 | Bromide |
| 3 | 3.468 | 0.0191 | 0.154 | Nitrate |
| 4 | 4.402 | 0.2589 | 2.106 | Phosphate |
| 5 | 15.682 | 275.3675 | 771.120 | DMDS |

62 minutes after the first measurement (Comparative Example 1), the area value for the determination of dimethyl disulphide was actually 21.9% below the starting value.

Comparative Experiments 1 to 4 show that amperometric detection at constant voltage is basically unsuitable for reproducible and reliable determination of dialkyl disulphides in alkanesulphonic acids and particularly of dimethyl disulphides in methanesulphonic acid.

III. Pulsed Amperometric Detection

By means of pulsed amperometric detection, dimethyl disulphide in a sample from the preparation of methanesulphonic acid by oxidation of dimethyl disulphide was determined over a period of more than one hour.

An analyte was used for this purpose (referred to as analyte B below), which was provided by dissolving 3 drops of the sample from the methanesulphonic acid preparation in 100 mL of a mixture of acetonitrile and water (ratio by volume 30:70).

The same instrumental arrangement was used as for the amperometric detection at constant voltage. The injection volume was 20 μl and the temperature of the separating column was about 25° C.

The electrooxidation potential had a value of 1.15 V and a duration of 300 ms, with a measurement duration of 100 ms. The cleaning potential had a value of 1.5 V and a duration of 50 ms, and the conditioning potential had a value of 0.1 V and a duration of 200 ms. The total duration of a measurement cycle was therefore 550 ms.

Example 1

At time t=0 min, the analyte B was injected into the ion chromatograph. The parameters for the ion chromatography conducted were:
Eluent: MeOH:$H_2O$ (3:7)+4.2 g/l $KH_2PO_4$+0.2 g/l $H_3PO_4$
Flow rate: 1.2 ml/min
Pressure: 160.1 bar
Recording duration: 25.0 min The components determined in the eluate of this ion chromatography are listed in table 5 and the chromatogram of this determination is shown in FIG. 5. The numbers of the peaks in this table correspond to the correspondingly numbered peaks in the chromatogram of FIG. 5.

TABLE 5

Results of the determination in Example 1

| Peak No. | Retention time [min] | Area (nA) * min | Height [nA] | Component |
|---|---|---|---|---|
| 1 | 1.631 | 3.7303 | 17.486 | Fluoride |
| 2 | 4.390 | 5.6792 | 48.794 | Phosphate |
| 3 | 6.644 | 0.2156 | 1.330 | MMTS |
| 4 | 15.716 | 333.7089 | 771.120 | DMDS |

Example 2

At time t=42 min, the analyte B was injected into the ion chromatograph. The parameters for the ion chromatography conducted were:
Eluent: MeOH:$H_2O$ (3:7)+4.2 g/l $KH_2PO_4$+0.2 g/l $H_3PO_4$
Flow rate: 1.2 ml/min
Pressure: 161.2 bar
Recording duration: 21.7 min The components determined in the eluate of this ion chromatography are listed in table 6 and the chromatogram of this determination is shown in FIG. 6. The numbers of the peaks in this table correspond to the correspondingly numbered peaks in the chromatogram of FIG. 6.

TABLE 6

Results of the determination in Example 2

| Peak No. | Retention time [min] | Area (nA) * min | Height [nA] | Component |
|---|---|---|---|---|
| 1 | 3.620 | 0.7375 | 6.608 | Nitrate |
| 2 | 4.985 | 0.2138 | 1.922 | Phosphate |
| 3 | 15.689 | 327.0947 | 825.014 | DMDS |

Example 3

At time t=2.5 h, the analyte B was injected into the ion chromatograph. The parameters for the ion chromatography conducted were:
Eluent: MeOH:$H_2O$ (3:7)+4.2 g/l $KH_2PO_4$+0.2 g/l $H_3PO_4$
Flow rate: 1.2 ml/min
Pressure: 161.2 bar
Recording duration: 21.7 min The components determined in the eluate of this ion chromatography are listed in table 7 and the chromatogram of this determination is shown in FIG. 7. The numbers of the peaks in this table correspond to the correspondingly numbered peaks in the chromatogram of FIG. 7.

TABLE 7

Results of the determination in Example 3

| Peak No. | Retention time [min] | Area (nA) * min | Height [nA] | Component |
|---|---|---|---|---|
| 1 | 1.576 | 0.4106 | 8.942 | Fluoride |
| 2 | 3.629 | 0.4906 | 4.236 | Nitrate |
| 3 | 4.994 | 0.2911 | 1.955 | Phosphate |
| 4 | 15.652 | 332.5320 | 811.847 | DMDS |

DISCUSSION OF THE MEASUREMENT RESULTS

The accuracy of pulsed amperometric detection was assessed using the values for the area under the peaks for dimethyl disulphide determined in Examples 1 to 3. This is because this value is an indication of the concentration of the dimethyl disulphide to be determined.

The area values determined in Examples 1 and 2 only differed from each other by 1.98%. The difference in the area values for Examples 1 and 3, which are the furthest apart from one another in time, was actually only 0.35%. Since the values determined in Examples 1 and 3 were virtually identical, pulsed amperometric detection therefore permits reliable determination of dimethyl disulphide. The difference that occurred in Example 2 is not therefore attributable to any lack of reproducibility of the measurement results, but to a measurement error.

The dimethyl disulphide concentration determined in this example was identical to that from Example 1. Moreover, the difference from the area value determined in Example 1 was only 0.35%, which is still significantly below the already small measurement error of Example 2. Compared to Comparative Examples 2 to 4, the differences in respect of the area value in Examples 2 and 3 are considerably lower, and, moreover, over a period more than twice as long as the total measurement duration in the comparative examples. Consequently, pulsed amperometric detection represents a reliable and reproducible determination of dimethyl disulphide in methanesulphonic acid.

IV. Comparison of Ion Chromatography and Pulsed Amperometry with NMR

Since it has been shown that pulsed amperometric detection is a suitable method for reproducible and reliable determination of dialkyl disulphides in alkanesulphonic acids, particularly of dimethyl disulphide in methanesulphonic acid, the accuracy of this method was compared with nuclear spin resonance.

Example 4

The same instrument arrangement as above was used as for the amperometric detection at constant voltage. A mixture of 3 drops of a sample from the preparation of methanesulphonic acid by oxidation of dimethyl disulphide in 100 ml of a mixture of acetonitrile and water (30:70 v/v) was used as analyte. The volume injected into the ion chromatograph was 20 µl, and the temperature of the separating column was about 25° C.
Eluent: MeOH:$H_2O$ (3:7)+4.2 g/l $KH_2PO_4$+0.2 g/l $H_3PO_4$
Flow rate: 1.2 ml/min
Pressure: 162.3 bar
Recording duration: 25.0 min The components determined in the eluate of this ion chromatography are listed in table 8 and the chromatogram of this determination is shown in FIG. 8. The numbers of the peaks in this table correspond to the correspondingly numbered peaks in the chromatogram of FIG. 8.

TABLE 9

Results of the determination in Comparative Example 5

| Peak No. | Component | Integral | Factor | Corrected integral | Ratio [mol %] | Amount [mmol] | Molar mass [g/mol] | Mass [mg] | Content [% by wt.] |
|---|---|---|---|---|---|---|---|---|---|
|   | Naphthalene | 464.047 | 4 | 116.012 | 53.0 | 0.305 | 128.16 | 39.07 | — |
| 1 | MA | 300.000 | 3 | 100.000 | 45.7 | 0.263 | 96.11 | 25.26 | 93.7 |
| 2 | DMDS | 16.952 | 6 | 2.825 | 1.3 | 0.007 | 94.20 | 0.70 | 2.6 |

TABLE 8

Results of the determination in Example 5

| Peak No. | Retention time [min] | Area (nA) * min | Height [nA] | Concentration [% by wt.] | Component |
|---|---|---|---|---|---|
| 1 | 1.686 | 2.3189 | 8.449 | — | MA |
| 2 | 3.510 | 2.5620 | 12.960 | — | Nitrate |
| 3 | 15.926 | 190.6092 | 430.759 | 2.567 | DMDS |

Comparative Example 5

Dimethyl disulphide in methanesulphonic acid was also determined by means of nuclear spin resonance. The analyte used for this determination was composed of 26.95 mg of a sample from the preparation of methanesulphonic acid by oxidation of dimethyl disulphide and 39.16 mg of naphthalene, and the latter compound served as solvent due to its inert character with respect to dimethyl disulphide and methanesulphonic acid. The nuclear spin resonance measurement was conducted with a 600 MHz Bruker Avance (III) spectrometer from Bruker Niospin, equipped with a Bruker Ascend 600 MHz magnet system from Bruker Biospin and a Prodigy CryoProbe probe head, and using MeOD as deuterated solvent. The measurement time was 20 minutes. The proton spectrum of this measurement is shown in FIG. 9, and the results obtained from this spectrum are summarized in Table 9.

Nuclear spin resonance allows the determination of dimethyl disulphide with a precision of one decimal place or 0.1% by weight, while pulsed amperometric detection enables determination of dimethyl disulphide up to 3 decimal places or 0.001% by weight, which represents greater precision by a factor of 100.

The dimethyl disulphide concentration determined in Examples 1 to 5 and in Comparative Example 5 always refers to the concentration of this component in the respective analyte. Since this analyte, however, constituted a dilution of the sample from the methanesulphonic acid preparation, the actual concentration of the dimethyl disulphide in this sample was higher by the dilution factor. Consequently, the differences between NMR analysis and pulsed amperometric detection were more notable in more concentrated samples. Because its accuracy is better by about a factor of 100 compared to NMR analysis, pulsed amperometric detection is therefore the method of choice for determination of a dialkyl disulphide in an alkanesulphonic acid.

V. Comparison of the Pulsed Amperometric Detector with a UV Detector

The higher sensitivity of the (pulsed) amperometric detector for a dialkyl disulphide in an alkanesulphonic acid was shown by a measurement series with a dilution series of dimethyl disulphide in methanesulphonic acid.

1. Sample Preparation:

The samples were composed of the weights according to Table 10, which were weighed out on a four-figure analytical balance. For calibration in the ppm range, one drop of the sample was weighed into 100 g of ultrapure water. A liquid sample was placed in a 4 ml volume sample vial (Rotilabor) and then closed with a screw cap with seal. The sample was then placed into the sample rack of the 858 Professional Sample Processor. The further dilution of the sample was carried out with the sample handler. This was effected in a mixing vessel with magnetic stirrer, with dilution of the sample in a ratio of 1:100. The sample was then pumped into one or more sample loops of different lengths. In an 882 Compact IC plus ion chromatograph, equipped with a column of the Gemini 5U C6-Phenyl 110A 250/4.6 type, the sample loop had a length of 20 μl. This was followed by cleaning steps for the mixing vessel for the next analysis.

2. Deviations/Errors:

A deviation of about 2% is within the scope of accuracy of ion chromatography. For the determination of dimethyl disulphide calibrations in the order of magnitude of 50 ppm were possible, and for the determination of S-methyl methanesulphonate, also known as methyl methanethiosulphonate (MMTS), calibrations in the order of magnitude of 100 ppm are possible. At even lower concentrations, the errors were significantly greater than the acceptable deviation of 2%.

3. Results

An 882 Compact IC plus (No. 2.850.9110 from Metrohm) ion chromatograph was used, equipped with a Vario 944 (No. 2.944.0010 from Metrohm) UV/VIS detector, an IC Amperometric Detector (No. 2.850.9110 from Metrohm) and a pressure gauge, the purpose of which was to enable monitoring of a constant pressure during the spectral recording.

4 experiments were conducted with the entries stated in Table 10 for the respective analytes.

TABLE 10

Summary of the analytes and the measurement results

| Experiment | Component | Weight | Nominal value % | Actual value % | Deviation % | Detector |
|---|---|---|---|---|---|---|
| 1 | MA | 45.77 | 90.05 | 90 | 0.06 | LF |
|  | MMTS | 1.95 | 3.84 | 3.849 | 0.12 | UV 210 |
|  | DMDS | 3.10 | 6.10 | 6.108 | 0.08 | AD |
|  |  |  |  | 6.109 | 0.10 | UV 210 |
| 2 | MA | 47.56 | 95.00 | 94.33 | −0.07 | LF |
|  | MMTS | 0.99 | 1.98 | 1.941 | −1.75 | UV 210 |
|  | DMDS | 1.52 | 3.03 | 3.011 | −0.57 | AD |
|  |  |  |  | 3.007 | −0.70 | UV 210 |
| 3 | MA | 49.14 | 97.98 | 97.79 | −0.19 | LF |
|  | MMTS | 0.5179 | 1.0320 | 1.079 | 4.56 | UV 210 |
|  | DMDS | 0.4976 | 0.9921 | 0.996 | 0.40 | AD |
|  |  |  |  | 1 | 0.80 | UV 210 |
| 4 | MA | 49.66 | 99.28 | 99.40 | 0.13 | LF |
|  | MMTS | 0.1108 | 0.2214 | 0.19 | −14.19 | UV 210 |
|  | DMDS | 0.2519 | 0.5034 | 0.518 | 2.89 | AD |
|  |  |  |  | 0.521 | 3.49 | UV 210 |

The measurement results summarized in table 10 show that a (pulsed) amperometric detector 5 is superior to a UV/VIS spectrometer with respect to the precision in the determination of dimethyl disulphide. This greater precision of (pulsed) amperometry in the determination of dimethyl disulphide actually increases still further with increasing dilution of the dimethyl disulphide in the methanesulphonic acid.

The invention claimed is:

1. A process for preparing an alkanesulphonic acid, the process comprising:
   a) oxidizing at least one sulphur-containing starting compound with an oxidizing agent, thereby producing a corresponding alkanesulphonic acid, wherein the at least one sulphur-containing starting compound is selected from the group consisting of alkyl mercaptan, dialkyl disulphide and dialkyl polysulphide having three to nine sulphur atoms,
   b) determining the at least one sulphur-containing starting compound and/or at least one oxidation intermediate from the oxidizing the at least one sulphur-containing starting compound to the corresponding alkanesulphonic acid in a reaction output from the oxidizing, wherein the at least one oxidation intermediate is determined to be an S-alkyl alkanesulfonate and is determined with UV-vis spectroscopy, and the at least one sulphur-containing starting compound is determined to be a dialkyl disulphide and/or a dialkyl polysulphide and is determined by pulsed amperometric detection, and
   c) supplying an additional oxidizing agent in the oxidizing to complete a oxidation reaction after the determining.

2. The process according to claim 1, wherein the at least one oxidation intermediate and the at least one sulphur-containing starting compound are independently determined in separate samples from the reaction output.

3. The process according to claim 1, further comprising:
   prior to the determining, performing a chromatographic separation of a sample from the reaction output.

4. The process according to claim 1, wherein the oxidizing agent is an oxidizing agent with free oxygen and/or with oxygen in bound form.

5. The process according to claim 1, wherein the oxidizing is conducted in at least one reactor.

6. The process according to claim 5, wherein the oxidizing is conducted in at least two reactors arranged in series.

7. The process according to claim 5, wherein the determining and optionally the supplying is conducted downstream of a first reactor and
   if more than two reactors arranged in series are present, the determining and optionally the supplying is conducted downstream of a second reactor and each reactor thereafter.

8. The process according to claim 6,
   wherein the oxidizing in a first reactor is conducted with free oxygen and
   if more than two reactors arranged in series are present, oxygen in bound form is optionally fed into a second reactor and each reactor thereafter.

9. A method for preparing at least one alkanesulphonic acid, the method comprising:
   preparing the at least one alkanesulphonic acid with UV-vis spectroscopy and/or pulsed amperometric detection.

10. An apparatus for conducting at least one oxidation reaction, the apparatus comprising:
    i) a reactor for oxidizing at least one starting compound,
    ii) a measuring unit, downstream of the reactor, for determining at least one nonoxidized starting compound and/or at least one oxidation intermediate from the oxidation reaction of the at least one starting compound to a desired target compound in a reaction output from the oxidization reaction, wherein the measuring unit is a UV-Vis spectrometer and/or an amperometric detector, and
    iii) a unit, in contact with the measuring unit, for supplying additional oxidizing agent to the reactor.

11. The process according to claim 1, wherein the at least one sulphur-containing starting compound is selected from the group consisting of alkyl mercaptan of formula R—SH, dialkyl disulphide of formula R—S—S—R, and dialkyl polysulphide of formula R—S$_n$—R with n=3 to 9, wherein R is alkyl group.

12. The process according to claim 1, wherein the alkyl mercaptan, dialkyl disulphide and/or dialkyl polysulphide have linear or branched alkyl groups, each having 1 to 12 carbon atoms.

13. The process according to claim 1, wherein the alkyl groups are selected from the group consisting of methyl, ethyl, n-propyl, iso-propyl, n-butyl, iso-butyl and tert-butyl.

14. The process according to claim 1, wherein the sulphur-containing starting compound is methyl mercaptan, dimethyl disulphide and/or dimethyl polysulphide having three to nine sulphur atoms, and the alkanesulphonic acid to be prepared is methanesulphonic acid.

15. The process according to claim 1, wherein, if the sulphur-containing starting compound is dimethyl disulphide and/or dimethyl polysulphide, the process comprises preceding the oxidizing by preparing dimethyl disulphide and/or dimethyl polysulphide.

16. The process according to claim 15, wherein the dimethyl disulphide and/or dimethyl polysulphide is prepared by reacting methyl mercaptan with elemental sulphur.

17. The process according to claim 16, wherein hydrogen sulphide is formed and fed into the process for preparation of methyl mercaptan.

* * * * *